US008449908B2

(12) United States Patent
Stinchcomb et al.

(10) Patent No.: US 8,449,908 B2
(45) Date of Patent: May 28, 2013

(54) TRANSDERMAL DELIVERY OF CANNABIDIOL

(75) Inventors: Audra L. Stinchcomb, Lexington, KY (US); Buchi N. Nalluri, Lexington, KY (US)

(73) Assignee: Alltranz, LLC, Lexington, KY (US)

( * ) Notice: Subject to any disclaimer, the term of this patent is extended or adjusted under 35 U.S.C. 154(b) by 1546 days.

(21) Appl. No.: 11/157,034

(22) Filed: Jun. 20, 2005

(65) Prior Publication Data

US 2005/0266061 A1    Dec. 1, 2005

(51) Int. Cl.
*A61F 13/00* (2006.01)
*A61F 13/02* (2006.01)
*A61K 9/70* (2006.01)
*A61L 15/16* (2006.01)

(52) U.S. Cl.
USPC ............................ 424/449; 424/448; 424/443

(58) Field of Classification Search
None
See application file for complete search history.

(56) References Cited

U.S. PATENT DOCUMENTS

| | | |
|---|---|---|
| 3,968,125 A | 7/1976 | Archer |
| 4,206,225 A | 6/1980 | Johnson |
| 4,232,018 A | 11/1980 | Johnson |
| 4,235,913 A | 11/1980 | Johnson et al. |
| 4,243,674 A | 1/1981 | Bindra |
| 4,260,764 A | 4/1981 | Johnson |
| 4,263,438 A | 4/1981 | Althuis et al. |
| 4,270,005 A | 5/1981 | Althuis et al. |
| 4,283,569 A | 8/1981 | Althuis et al. |
| 4,371,720 A | 2/1983 | Johnson et al. |
| 4,663,474 A | 5/1987 | Urban |
| 4,876,276 A | 10/1989 | Mechoulam et al. |
| 5,059,426 A * | 10/1991 | Chiang et al. ................. 424/449 |
| 5,223,262 A | 6/1993 | Kim et al. |
| 5,254,346 A | 10/1993 | Tucker et al. |

(Continued)

FOREIGN PATENT DOCUMENTS

| | | |
|---|---|---|
| EP | 0570920 A1 | 5/1992 |
| EP | 0656354 B1 | 12/1993 |

(Continued)

OTHER PUBLICATIONS

"Cannabinoid system as a potential target for drug development in the treatment of cardiovascular disease" by Mendizabal et al., Current Vascular Pharmacology, 2003, vol. 1, No. 3, 301-313.*

(Continued)

*Primary Examiner* — Isis Ghali
(74) *Attorney, Agent, or Firm* — Foley & Lardner LLP

(57) ABSTRACT

The present invention overcomes the problems associated with existing drug delivery systems by delivering cannabinoids transdermally. Preferably, the cannabinoids are delivered via an occlusive body (i.e., a patch) to alleviate harmful side effects and avoid gastrointestinal (first-pass) metabolism of the drug by the patient. A first aspect of the invention provides a method for relieving symptoms associated with illness or associated with the treatment of illness in a mammalian subject, comprising the steps of selecting at least one cannabinoid from the group consisting of cannabinol, cannabidiol, nabilone, levonantradol, (−)-HU-210, (+)-HU-210, 11-hydroxy-$\Delta^9$-THC, $\Delta^8$-THC-11-oic acid, CP 55,940, and R(+)-WIN 55,212-2, selecting at least one permeation enhancer from the group consisting of propylene glycol monolaurate, diethylene glycol monoethyl ether, an oleoyl macrogolglyceride, a caprylocaproyl macrogolglyceride, and an oleyl alcohol, and delivering the selected cannabinoid and permeation enhancer transdermally to treat an illness.

6 Claims, 12 Drawing Sheets

U.S. PATENT DOCUMENTS

| | | | |
|---|---|---|---|
| 5,310,561 | A | 5/1994 | Jao et al. |
| 5,521,215 | A | 5/1996 | Mechoulam et al. |
| 5,716,928 | A | 2/1998 | Benet et al. |
| 5,804,592 | A | 9/1998 | Volicer |
| 5,847,128 | A | 12/1998 | Martin et al. |
| 6,017,919 | A | 1/2000 | Inaba et al. |
| 6,028,084 | A | 2/2000 | Barth et al. |
| 6,100,259 | A | 8/2000 | Xiang et al. |
| 6,113,940 | A | 9/2000 | Brooke et al. |
| 6,132,762 | A | 10/2000 | Cristobal |
| 6,162,829 | A | 12/2000 | Burstein |
| 6,274,635 | B1* | 8/2001 | Travis .......................... 514/718 |
| 6,294,192 | B1* | 9/2001 | Patel et al. .................... 424/451 |
| 6,328,992 | B1 | 12/2001 | Brooke et al. |
| 6,503,532 | B1 | 1/2003 | Murty et al. |
| 2002/0111377 | A1* | 8/2002 | Stinchcomb ................. 514/468 |
| 2003/0158191 | A1 | 8/2003 | Travis |
| 2003/0166727 | A1 | 9/2003 | Mechoulam et al. |
| 2009/0036523 | A1 | 2/2009 | Stinchcomb et al. |

FOREIGN PATENT DOCUMENTS

| | | | |
|---|---|---|---|
| EP | 0656354 | A1 | 7/1994 |
| EP | 0885889 | A3 | 12/1995 |
| EP | 0860168 | A2 | 2/1997 |
| EP | 0799188 | B1 | 9/1999 |
| EP | 0868420 | B1 | 3/2000 |
| EP | 0670826 | B1 | 4/2000 |
| GB | 2439393 | A | 12/2007 |
| JP | 10236978 | A | 9/1998 |
| JP | 11080124 | A | 3/1999 |
| WO | WO 89/07959 | | 9/1989 |
| WO | WO 97/19063 | | 5/1997 |
| WO | WO 97/21682 | | 6/1997 |
| WO | WO 97/29079 | | 8/1997 |
| WO | WO 98/31227 | | 7/1998 |
| WO | WO 9832441 | | 7/1998 |
| WO | WO 9841519 | | 9/1998 |
| WO | WO 9902499 | | 1/1999 |
| WO | WO 9924471 | | 5/1999 |
| WO | WO 99/53917 | | 10/1999 |
| WO | WO 0016756 | | 3/2000 |
| WO | WO 0032200 | | 6/2000 |
| WO | WO 0040562 | | 7/2000 |
| WO | 2004/039317 | A2 | 5/2004 |
| WO | 2004/082620 | A2 | 9/2004 |
| WO | 2006/133941 | A2 | 12/2006 |
| WO | 2007/001891 | A1 | 1/2007 |
| WO | 2008/107879 | A1 | 9/2008 |
| WO | 2009/018389 | A1 | 2/2009 |

OTHER PUBLICATIONS

Welch et al. The article "Synergistic interactions of endogenous opioids and cannabinoids systems", Brain Research 848 (1999) 183-190.*

International Search Report for PCT/US06/23387, Nov. 7, 2006.

Written Opinion of the International Searching Authority for PCT/US06/23387, Nov. 7, 2006.

Lichtman, A.H., "SR 141716A Enhances Spatial Memory as Assessed in a Radial-Arm Maze Task in Rats," European Journal of Pharmacology, vol. 404, Sep. 15, 2000, pp. 175-179.

Oz et al., "Endogenous Cannabinoid Anandamide Directly Inhibits Voltage-Dependent Ca(U2)U+ Fluxes in Rabbit T-Tubule Membranes," European Journal of Pharmacology, vol. 404, Sep. 15, 2000, pp. 13-20.

Cheer et al., "Lack of Response Suppression Follows Repeated Ventral Tegmental Cannabinoid Administration: an In Vitro Electrophysiological Study," Neuroscience, vol. 99, No. 4, Aug. 23, 2000, pp. 661-667.

Han et al., "A Performance-Dependent Adjustment of the Retention Interval in a Delayed Non-Matching-to-Position Paradigm Differentiates Effects of Amnestic Drugs in Rats," European Journal of Pharmacology, vol. 403, Sep. 1, 2000, pp. 87-93.

Harris et al., "Spinal Anandamide Inhibits Nociceptive Transmission via Cannabinoid Receptor Activation in Vivo," NeuroReport, vol. 11, No. 12, Aug. 21, 2000, pp. 2817-2819.

Salzet et al., "Comparative Biology of the Endocannabinoid System: Possible Role in the Immune Response," European Journal of Biochemistry, vol. 267, 2000, pp. 4917-4927.

Mie et al., "Influence of the N-1 Alkyl Chain Length of Cannabimimetic Indoles Upon CB$D1 and CB$D2 Receptor Binding," Drug and Alcohol Dependence, vol. 60, Aug. 1, 2000, pp. 133-140.

Nocerino et al., "Cannabis and Cannabinoid Receptors," Fitoterapia, vol. 71, Aug. 1, 2000, pp. S6-S12.

Denovan-Wright et al., "Cannabinoid Receptor Messenger RNA Levels Decrease in a Subset of Neurons of the Lateral Striatrum, Cortex and Hippocampus of Transgenic Huntington's Disease Mice," Neuroscience, vol. 98, No. 4, Jul. 12, 2000, pp. 705-713.

No-Author Listed, "Lifegroup's Breakthrough in Inflammation Annotated Title-Researchlife Unit of Lifegroup Makes Major Inflammation Find that Mast Cells Express Peripheral Cannabinoid Receptor that Exhibit Differential Sensitivity to Anandamide & Palmitoylethanolamide," Pharmaceutical Business News, No. 242, May 12, 1995, p. 15.

Baker et al., "Cannabinoids Control Spasticity and Tremor in a Multiple Sclerosis Model, "Nature (London) vol. 404, Mar. 2000, pp. 84-87.

Pertwee, R.G., "Neuropharmacology and Therapeutic Potential of Cannabinoids," Addiction Biology, vol. 5, No. 1, 2000, pp. 37-46.

Sepe et al., "Bioactive Long Chain N-Acylethanolamines in Five Species of Edible Bivalve Molluscs. Possible Implications for Mollusc Physiology and Sea Food Industry," Biochimica et Biophysica Acta, Lipids and Lipid Metabolism, vol. 1389, No. 2, 1998, pp. 101-111.

Wang et al., "Stage-Specific Excitation of Cannabinoid Receptor Exhibits Differential Effects on Mouse Embryonic Development," Biology of Reproduction, vol. 60, 1999, pp. 839-844.

Van Zadelhoff et al., "With Anandamide as Substrate Plant 5-Lipoxygenases Behave Like 11-Lipoxygenases," Biochemical and Biophysical Research Communications, vol. 248, No. 1, 1998, pp. 33-38.

Arthur, C., "Body's Pain Relief Mimics Cannabis," The Independent, UK, vol. 98, No. 572, Jul. 16, 1998.

Page et al., "Effects of Systemic 3-Nitropropionic Acid-Induced Lesions of the Dorsal Striatum on Cannabinoid and Mu-Opioid Receptor Binding in the Basal Ganglia," Experimental Brain Research YExp. Brain Res., vol. 130, No. 2, 2000, pp. 142-150.

Shen et al., "Cannabinoid Receptor Agonists Protect Cultured Rat Hippocampal Neurons from Excitotoxicity," Molecular Pharmacology, vol. 54, No. 3, 1998, pp. 459-462.

Williams et al., "Anadamide Induces Overeating: Mediation by Central Cannabinoid (CB1) Receptors," Psychopharmacology, vol. 143, No. 3, 1999, pp. 315-317.

Richardson et al., "SR 141716A, A Cannabinoid Receptor Antagonist, Produces Hyperalgesia in Untreated Mice," European Journal of Pharmacology, vol. 319, No. 2-3, 1997, pp. R3-R4.

Guiliani et al., "Effects of the Cannabinoid Receptor Agonist, HU 210, on Ingestive Behaviour and Body Weight of Rats," European Journal of Pharmacology, vol. 391, No. 3, Mar. 17, 2000, pp. 275-279.

Gallate et al., "Increased Motivation for Beer in Rats Following Administration of Cannabinoid CB1 Receptor Agonist," European Journal of Pharmacology, vol. 370, No. 3, Apr. 10, 1999, pp. 233-240.

Waksman et al., "The Central Cannabinoid Receptor (CB1) Mediates Inhibition of Nitric Oxide Production by Rat Microglial Cells," Journal of Pharmacology Exp. Ther., vol. 288, No. 3, Mar. 1999, pp. 1357-1366.

Romero et al., "Loss of Cannabinoid Receptor Binding and Messenger Rna Levels and Cannabinoid Agonist-Stimulated Y35S"Guanylyl-5'-O-(thio)-Triphosphate Binding in the Basal Ganglia of Aged Rats," Neuroscience, vol. 84, No. 4, Jun. 1998, pp. 1075-1083.

No-Author, "Anandamide May be Natural Ligand of Cannabinoid Receptor," Citation from Predicast F&S Index (PFS): PFS, Chemical & Engineering News, Dec. 21, 1992, p. 16.

Lyons-Johnson, D., "Cannabinoid Receptors Key to Stress Response," Citation from Prompt—Predicasts: PMT, Agricultural Research, vol. 45, No. 6, Jun. 1997, p. 15.

No-Author," Atlantic Report on Potent Analgesic/Anti-Inflammatory Agent Presented at International Conference on Prostaglandins and Related Compounds," Citation from Prompt—Predicasts: PMT, Business Wire, Sep. 24, 1996, p. 09241083.

Netzeband et al., "Cannabinoids Enhance NMDA-Elicited $Ca^{2+}$ Signals in Cerebellar Granule Neurons in Culture," Journal of Neuroscience, vol. 19, No. 20, Oct. 15, 1999, pp. 8765-8777.

Dajani et al., "1',1'-Dimethylheptyl-Δ-8-tetrahydrocannabinol-11-oic Acid: A Novel, Orally Effective Cannabinoid with Analgesic and Anti-inflammatory Properties," Journal of Pharmacology and Experimental Therapeutics, vol. 291, No. 1, 1999, pp. 31-38.

Memo to Field Communications Staff of the American Cancer Society Capital Region Media Relations, Jan. 2000.

Gormley, M., "Researchers Test 'Marijuana Patch'," Associated Press Release, Jan. 20 no year referenced.

"ACS Marijuana Patch Research Grant Q&A for American Cancer Society Staff and Volunteers," Statement taken from the Cancer Information Database on Lotus Notes, Jan. 20, 1999.

Pugh, Jr., G. et al., "The Roles of Endogenous Opioids in Enhancing the Antinociception Produced by the Combination of the Delta-9 Tetrahydrocannabinol and Morphine in the Spinal Cord," The Journal of Pharmacology and Experimental Therapeutics, vol. 279, No. 2, 1996, pp. 608-616.

Bronaugh, R. L., "In Vitro Viable Skin Model" *Models for Assessing Drug Absorption and Metabolism*, vol. 8, Chapter 20, Plenum Press, 1996, pp. 375-386.

Pop, E. et al., "Derivatives of Dexanabinol. I. Water-soluble Salts of Glycinate Esters," Pharmaceutical Research, vol. 43, No. 1, 1996, pp. 62-69.

Stinchcomb, A. L. et al., "A solubility and Related Physicochemical Property Comparison of Buprenorphine and Its 3-Alkyl Esters," Pharmaceutical Research, vol. 12, No. 10, 1995, pp. 1526-1529.

Potts, R. O. et al., "A Predictive Algorithm for Skin Permeability: The Effects of Molecular Size and Hydrogen Bond Activity," Pharmaceutical Research, vol. 12, No. 11, 1995, pp. 1628-1633.

Abraham, M. H. et al., "The Factors that Influence Skin Penetration of Solutes," J. Pharm. Parmacol., vol. 47, 1995, pp. 8-16.

Lien, E. J. et al., "QSAR Analysis of Skin Permeability of Various Drugs in Man as Compared to in Vivo and in Vitro Studies in Rodents," Pharmaceutical Research, Vo. 12, No. 4, 1995, pp. 583-587.

Abrahamov, A. et al., "An Efficient New Cannabinoid Antiemetic in Pediatric Oncology," Life Sciences, vol. 56, Nos. 23/24, 1995, pp. 2097-2102.

Mattes, R. D. et al., "Cannabinoids and Appetite Stimulation," Pharmacology Biochemistry and Behavior, vol. 49, No. 1, 1994, pp. 187-195.

Nelson, K. et al., "A Phase II Study of Delta-9-Tetrahydrocannabinol for Appetite Stimulation in Cancer-Associated Anorexia," Journal of Palliative Care, vol. 10, No. 1, 1994, pp. 14-18.

Debruyne, D. et al., "Comparison of Three Advanced Chromatographic Techniques for Cannabis Identification," Bulletin of Narcotics, vol. XLVI, No. 2, 1994, pp. 109-121.

Liu, P. et al., "Transport of Beta-Estradiol in Freshly Excised Human Skin in Vitro: Diffusion and Metabolism in Each Skin Layer," Pharmaceutical Research, vol. 11, No. 12, 1994, pp. 1777-1784.

Bornehim, L. M. et al., "Characterization of Cannabidiol-Mediated Cytochrom P450 Inactivation," Biochemical Pharmacology, vol. 45, No. 6, 1993, pp. 1323-1331.

Abraham, M. H. "Application of Solvation Equations to Chemical and Biochemical Processes," Pure and Applied Chemistry, vol. 65, No. 12, 1993, pp. 2503-2512.

Gerostamoulos, J. et al., "Incidence of Psychoactive Cannabinoids in Drivers Killed in Motor Vehicle Accidents," Journal of Forensic Sciences, JFSCA, vol. 38, No. 3, May 1993, pp. 649-656.

Potts, R O. et al., "Predicting Skin Permeability," Pharmaceutical Research, vol. 9, No. 5, 1992, pp. 663-669.

No-Author Listed, "Potential Rolse of Cannabinoids for Therapy of Neurological Disorders," *Marijuana/Cannabinoids Neurobiology and Neurophysiology*, L. Murphy and A. Bartke, Editors, CRC Press, 1992, pp. 459-524.

Bornheim, L M. et al., "Human Hepatic Microsomal Metabolism of Delta-1-Tetrahydrocannabinol," Drug Metabolism and Disposition, vol. 20, No. 2, 1992, pp. 241-246.

Plasse, T. F. et al., "Recent Clinical Experience With Dronabinol-1," Pharmacology Biochemistry & Behavior, vol. 40, 1991, pp. 695-700.

Collier, S. W. et al., "Cutaneous Metabolism," *In Vitro Percutaneous Absorption: Principles and.Fundamentals, and Applications*, R. L. Bronaugh and H. I. Maibach, Editors, CRC Press, 1991, pp. 67-88.

Levitz, S. M. et al., "Aspergillosis and Marijuana," Annals of Internal Medicine, vol. 115, No. 7, Oct. 1, 1991, pp. 578-579.

Tayar, N. E. et al., "Percutaneous Penetration of Drugs: A Quantitative Structure—Permeability Relationship Study," Journal of Pharmaceutical Sciences, vol. 8, No. 8, Aug. 1991, pp. 744-749.

Thomas, B. F. et al., "In Vitro Metabolism of (−)-cis-3-[2-hydroxy-4-(1,1-dimethylheptyl) phenyl]-trans4-(3-hydroxypropyl) Cyclohexanol, A Synthetic Bicyclic Cannabinoid Analog," Drug Metab Dispos, vol. 18, No. 6, Nov.-Dec. 1990, pp. 1046-1054.

Koa, J. et al., "Cutaneous Metabolism of Xenobiotics," Drug Metabolism Reviews, vol. 22, No. 4, 1990, pp. 363-410.

Flynn, G. L. "Physiochemical Determinants of Skin Absorption," *Principals of Route-to-Route Extrapolation for Risk Assessment*, T. R. Gerrity and C. J. Henry, Editors, 1990, pp. 93-127.

Anderson, B. D. et al., "Solute Structure-Permeability Relationships in Human Stratum Comeium," The Society for Investigative Dermatology, Inc., 1989, pp. 280-286.

Vinciguerra, V. et al., "Inhalation Marijuana as an Antiemetic for Cancer Chemotherapy," New York State Journal of Medicine, Oct. 1988, pp. 525-527.

Wu, T. C. et al., "Pulmonary Hazards of Smoking Marijuana as Compared with Tobacco," The New England Journal of Medicine, vol. 318, No. 6, Feb. 11, 2988, pp. 347-351.

Kasting, G. B. et al., "Effect of Lipid Solubility and Molecular Size on Percutaneous Absorption," Pharmacol. Skin, vol. 1, 1987, pp. 138-153.

Bronaugh, R. L. et al., "Methods for In Vitro Percutaneous Absorption Studies III: Hydrophobic Compounds," Joumal of Pharmaceutical Sciences, vol. 73, No. 9, Sep. 1984, pp. 1255-1258.

Jay, W. M. et al., "Multiple-Drop Study of Topically Applied 1% Delta-9-Tetrahydrocannabinol in Human Eyes," Arch Ophtalmol, vol. 101, Apr. 1983, pp. 591-593.

No-Author Listed, "Contamination of Marijuana Cigarettes with Pathogenic Bacteria—Possible Source of Infection in Cancer Patients," Cancer Treatment Reports, vol. 66, No. 3, Mar. 1982, pp. 589-591.

Taylor, D. N. et al., "Samonellosis Associated with Marijuana—A Multistate Outbreak Traced by Plasmid Fingerprinting," The New England Journal of Medicine, vol. 306, No. 21, 1982, pp. 1249-1253.

Shepard, R. M., "Pharmacokinetics of Levonantradol in Laboratory Animals and Man," Journal of Clinical Pharmacology, Aug-Sep; 21(8-9 Suppl): 190S-200S, 1981.

Bickers, D. R. et al., "Epidermis: A Site of Drug Metabolism of Neonatal Rat Skin, Studies on Cytochrome P-450 Content and Mixed Function Oxidase and Epoxide Hydrolase Activity," Molecular Pharmacology, vol. 21, Sep. 8, 1981, pp. 239-247.

Greene, D. E. et al., "Quantitation of a Delta-9-Tetrahydrocannabinol and Its Metabolites in Human Urine by Probability Based Matching GC/MS," *Cannabinoid Analysis in Physiological Fluids*, Vinson, JA Ed., American Chemical Society, 1979.

Chang, A. E. et al., "Delta-9 Tetrahydrocannibinol as an Antiemetic in Cancer Patients Receiving High-Dose Methotrexate," Annals of Internal Medicine, vol. 91, 1979, pp. 819-824.

Yu, C.D. et al., "Physical Model Evaluation of Topical Prodrug Delivery—Simultaneous Transport and Bioconversion of Vidarabine -5'—valerate I: Physical Model Development," Journal of Pharmaceutical Sciences, vol. 68, No. 11, Nov. 1979, pp. 1342-1346.

Rubin, A. et al., "Physiologic Disposition of Nabilone, a Cannabinol Derivative, in Man," Clinical Psychology and Therapeutics, vol. 22, No. 1, Mar. 5, 1977, pp. 85-91.

Tashkin, D. P. et al., "Broncial Effects of Aerosolized Delta-9-Tetrahydrocannabinol in Healthy and Asthmatic Subjects," American Review of Respiratory Disease, vol. 115, 1977, pp. 57-65.

Hansch, C. et al., "'Aromatic' Substituent Constants for Structure—Activity Correlations," Journal of Medicinal Chemistry, vol. 16, No. 11, 1973, pp. 1207-1213.

Lowry, O. H. et al., "Protein Measurement with the Folin Phenol Reagent," From the Department of Pharmacology, Washington University School of Medicine, St. Louis, Missouri, May 28, 1951, pp. 265-275.

Flynn, G.I. "Cutaneous and Transdermal Delivery. Process and Systems Delivery" *Modern Pharmaceutics*, Third Edition, pp. 239-298.

Hoffman, D. et al., "On the Carcinogenicity of Marijuana Smoke," *Recent Advances in Phytochemistry*, vol. 9, pp. 63-81.

No-Author Listed, "Dronabinol," *Product Identification Guide*, pp. 1083-1086.

"Therapeutic Uses of Cannabis," British Medical Association, Harwood Academic Publishers, 1997, pp. 10, 11, 26-45, 75-81.

Touitou, E. et al., "Transdermal Delivery of Tetrahydrocannabinol," International Journal of Pharmaceutics, vol. 43, 1988, pp. 9-15.

Touitou et al., "Altered Skin Permeation of a Highly Lipophilic Molecule: Tetrahydrocannabinol," International Journal of Pharmaceutics, vol. 43, 1988, pp. 17-22.

Novak, J. et al., "Cannabis XXIV. A New Convenient Synthesis of Cannabinol," Tetrahedron Letters, vol. 23, No. 2, 1982. pp. 253-254.

Mechoulam, R. et al., "A Total Synthesis of $dl$-$\Delta^1$-Tetrahydrocannabinol, the Active Constituent of Hashish," Journal of American Chemical Society, vol. 87, 1965, pp. 3273-3275.

Siegel, C. et al., "An Optically Active Terpenic Synthon for $\Delta^9$-Tetrahydrocannabinol (THC) and Its 1',1'-Dimethylheptyl Analogue," Journal of Organic Chemistry, vol. 54, 1989, pp. 5428-5430.

No Author Listed, "Institute of Medicine Report; What Marijuana Legalizers Won't Tell You: Substance Found in Marijuana Can Be Delivered Through Various Legal Means," PR Newswire Association, Inc., Mar. 17, 1999, pp. 1-2.

No Author Listed, "Institute of Medicine Report; ONDCP and IOM Agree That 'Chemically-Defined Drugs'—Like Marinol—Not Smoked Marijuana is the Future of Cannabinoid Drugs," PR Newswire Association, Inc., Mar. 17, 1999, pp. 1-2.

May 9, 2005 Final Office Action filed in U.S. Appl. No. 10/032,163.

Feb. 10, 2005 Amendment and Response filed in U.S. Appl. No. 10/032,163.

Sep. 10, 2004 Non-Final Office Action filed in U.S. Appl. No. 10/032,163.

Jul. 1, 2004 Request for Continued Examination filed in U.S. Appl. No. 10/032,163.

Mar. 2, 2004 Final Office Action filed in U.S. Appl. No. 10/032,163.

Dec. 22, 2003 Amendment and Response to Office Action filed in U.S. Appl. No. 10/032,163.

Sep. 23, 2003 Non-Final Office Action filed in U.S. Appl. No. 10/032,163.

International Search Report for PCT/US2008/071659, mailed on Dec. 12, 2008.

Written Opinion of the International Searching Authority for PCT/US2008/071659, mailed on Dec. 12, 2008.

"Institute of Medicine Releases Report on Medicinal Marijuana," Citation from Prompt—Predicasts: PMT, PR Newswife, Mar. 17, 1999.

FDA-approved product label for Marinol, 2006.

Abu-Lafi, et al., "Role of Hydroxyl Groups in Chiral Recognition of Cannabinoids by Carmbamated Amylose", J. Chromatography, vol. 679, pp. 47-58 (1994); XP002505687.

Adam, MD et al., "A cannabinoid with cardiovascular activity by no overt behavioral effects" 33(9) Experientia 1204-05 (1977).

Agu, et al., "Permeation of WIN 44,212-2, A Potent Cannabinoid Receptor Agonist, Across Human Trancheo-Broncial Tissue in Vitro and Rat Nasal Epithelium in Vivo", J. Pharmacy and Pharmacology, vol. 58, pp. 1459-1465 (2006).

Asasua Del Valle, "Implication fo Cannabinoids in Neurological Diseases", Cellular and Molecular Neurobiology, vol. 26, Nos. 4-6, pp. 579-591 (2006).

Alvarez, F. J. et al., (2008). "Neuroprotective Effects of the Nonpsychoactive Cannabinoid Cannabidiol in Hypoxic-Ischemic Newborn Piglets." Pediatric Researc 64(6): 653-658.

Aragona, M., et al., (2009). "Psychopathological and Cognitive Effects of Therapeutic Cannabinoids in Multiple Sclerosis: A Double-Bline, Placebo Controlled, Crossover Study," Clin Neuropharmacol.

Attal N. et al., (2004) "Are oral cannbinoids safe and effective in refractory neuropathic pain?" Eur J Pain 8: 173-177.

Barak V et al., (1992) "The M20 IL-1 inhibitor prevents onset of adjuvant arthritis." Biotherapy 4: 317-323.

Barnes, M. P. (2006, "Sativex (R): clinical efficacy and tolerablity in the treatment of symptoms of multiple sclerosis and neuropathic pain." Expert Opinion on Pharmacotherapy 7(5): 607-615.

Belgrave, B.E. et al., "The effect of cannabidiol, alone and in combination with ethanol, on human performance" Psychophamacology,64(2) (1979) p. 243-6.

Ben Amar, "Cannabinoids in Medicine: A Review of Their Therapeutic Potential", J. Ethnopharmacology 105, pp. 1-25 (2006).

Ben-Shabat, et al., "New Cannabidiol Derivatives: Synthesis, Binding to Cannabinoid Receptor, and Evaluation of Their Antiinflammatory Activity", J. Medicinal Chem., vol. 49, No. 3, pp. 1113-1117 (2006).

Berman, J. S. et al., (2004), "Efficacy of two cannabis based medicinal extracts for relief of central neuropathic pain from brachial plexus avulsion: results of a randomised controlled trial" Pain 112(3): 299-306.

Bird, K.D. et al., "Intercannabinoid and cannabinoid-ethanol interactions and their effects on human performance" Psychopharmacology (Berlin, Germany), 1980, 71(2): p. 181-8.

Bisogno, T. et al., (2001). "Molecular targets for cannabidiol and its synthetic analogues: effect on vanilloid VR1 receptors and on the cellular uptake and enzymatic hydrolysis of anandamide" Br J Pharmacol 134(4): 845-52.

Bisogno, et al., "The EndoCannabinoid Signaling System: Biochemical Aspects", Pharmacology, Biochem. And Behavior 81, pp. 224-238 (2005).

Blake, D. R. et al., (2006). "Preliminary assessment of the efficacy, tolerability and safety of a cannabis-based medicine (Sativex) in the treatment of pain caused by rheumatoid arthritis" Rheumatology (Oxford, England) 45(1): 50-2.

Bodo, et al., "A Hot New Twist to Hair Biology: Involvement of Vanilloid Receptor-1 (VR1/TRPV1) Signaling in Human Hair Growth Control", Amer. J. Pathology, vol. 166, No. 4, pp. 985-998 (Apr. 2005).

Bornheim, L.M. et al., "Effect of cannabidiol on cytochrome P-450 and hexobarbital sleep time" 30(5) Biochem. Pharmacology, pp. 503-507 (1981).

Bornheim, L. M. and M. A. Correia (1989). "Purification and characterization of a mouse liver cytochrome p. 450 induced by cannabidiol" Mol Pharmacol 36(3): 377-83.

Bornheim, L. M. and M. A. Correia (1990). "Selective inactivation of mouse liver cytochrome P-450IIIA by cannabidiol" Molecular Pharmacology 38(3): 319-26.

Bornheim, L. M. and M. A. Correia, "Purification and characterization of the major hepatic cannabinoid hydroxylase in the mouse: a possible member of the cytochrome P-450IIC subfamily" 40(2) Molecular Pharmacology 228-34 (1991).

Bornheim, L. M. et al., (1993). "Induction and genetic regulation of mouse hepatic cytochrome P450 by cannabidiol" Biochem Pharmacol 48(1): 161-71.

Bornheim, L. M. and M. P. Grillo (1998). "Characterization of Cytochrome P450 3A Inactivation by Cannabidiol: Possible Involvement of Cannabidiol-Hydroxyquinone as a P450 Inactivator" Chemical Research in Toxicology 11(10): 1209-1216.

Bornheim, L. M. et al., (1994). "The effect of cannabidiol on mouse hepatic microsomal cytochrome P450-dependent anandamide metabolism" Biochemical and Biophysical Research Communications 197(2): 740-6.

Borys, H. K. et al., (1979). "Development of tolerance to the prolongation of hexobarbitone sleeping time caused by cannabidiol" British J. Pharmacology 67(1): 93-101.

Braida, D. et al., (2003). "Post-ischemic treatment with cannabidiol prevents electroencephalographic flattening, hyperlocomotion and neuronal injury in gerbils." Neuroscience Letters 346(1-2): 61-4.

Bright, T.P. et al., "Cardiopulmonary effects of cannabidiol in anesthetized mongrel dogs" 31(3) Toxicology and Applied Pharmacology 520-26 (1975).

Brady, C. M. et al., (2004). "An open-label pilot study of cannabis-based extracts for bladder dysfunction in advanced multiple sclerosis." Multiple Sclerosis 10(4): 425-433.

Brown and Harvey, "In Vitro Metabolism of Cannabichromene in Seven Common Laboratory Animals", Drug Metabolism and Disposition, vol. 18, No. 6, pp. 1065-1070 (1990).

Buckwalter JA and Martin JA (2006) "Osteoarthritis" Adv Drug Deliv Rev 58: 150-167.

Burns and Ineck, "Cannabinoid Analgesia as a Potential New Therapeutic Option in the Treatment of Chronic Pain", Annals of Pharmacotherapy, vol. 40, pp. 251-260 (2006).

Burstein SH and Zurier RB, "Cannabinoids, endocannabinoids, and related analogs in inflammation" 11(1) AAPS 109-19 (2009).

Capasso, R. et al., (2008). "Cannabidiol, extracted from Cannabis sativa, selectively inhibits inflammatory hypermotility in mice" British J. Pharmacology 154(5): 1001-1008.

Carlini, E.A. and J.M. Cunha, "Hypnotic and antiepileptic effects of cannabidiol" J. Clinical Pharmacology, 1981. 21(8-9, Suppl.): p. 417-27.

Carney, J.M. et al., "Effects of systemic and intraventricular administration of cannabinoids on schedule-controlled responding in the squirrel monkey" J. pharmacology and experimental therapeutics, 1979. 210(3): p. 399-404.

Carrier, E. J. et al., (2006). "Inhibition of an equilibrative nucleoside transporter by cannabidiol: a mechanism of cannabinoid immunosuppression" Proc. Nat'l Acad. Sci. USA 103(20): 7895-900.

Challapalli, et al., "In Vitro Experiment Optimization for Measuring Tetrahydrocannabinol Skin Permeation", International J. Pharmaceutics 241, pp. 329-339 (2002).

Chang, M.C. and H. Schuel, "Reduction of the fertilizing capacity of sea urchin sperm by cannabinoids derived from marihuana. II. Ultrastructural changes associated with inhibition of the acrosome reaction" Molecular Reproduction and Development, 1991. 29(1): p. 60-71.

Clayton N. et al., (2002) "CB1 and CB2 cannabinoid receptors are implicated in inflammatory pain" Pain 96: 253-260.

Collin, C. et al., (2006). "A randomised controlled study of Sativex (R) in patients with symptoms of spasticity due to multiple sclerosis" Multiple Sclerosis 12: S111-S112 (abstract).

Collin, C. et al., (2007). "Randomized controlled trial of cannabis-based medicine in spasticity caused by multiple sclerosis" European J. Neurology 14(3): 290-296.

Collin, C. and P. Duncombe (2006). "Meta-analysis of the effects of Sativex (R) on spasticity associated with multiple sclerosis" Multiple Sclerosis 12: S13-S13 (abstract).

Collin, C. et al., (2007). "Results of an open-label extension trial of sativex (THC : CBD) in patients with multiple sclerosis and symptoms of spasticity" Multiple Sclerosis 13: S129-S129 (abstract).

Collin, C. et al., (2005). "A cannabis-based medicine (Sativex) has sustained efficacy in the treatment of spasticity in multiple sclerosis" J. Neurology Neurosurgery and Psychiatry 76(9): 1316-1316 (abstract).

Colombo et al., "Endocannabinoid System and Alcohol Addiction: Pharmacological Studies", Pharmacology Biochem. and Behavior vol. 81 pp. 369-380 (2005).

Comelli, F. et al., (2008). "Antihyperalgesic effect of a Cannabis sativa extract in a rat model of neuropathic pain: mechanisms involved" Phytotherapy research PTR 22(8): 1017-24.

Consroe, P. et al., (1991). "Assay of plasma cannabidiol by capillary gas chromatography/ion trap mass spectroscopy following high-dose repeated daily oral administration in humans" Pharmacology, Biochem., and Behavior 40(3): 517-22.

Consroe, P. et al., (1991). "Controlled clinical trial of cannabidiol in Huntington's disease" Pharmacology, Biochem., and Behavior 40(3): 701-8.

Consroe et al., "Effects of cannabidiol in animal models of neurological dysfunction," 7 Marijuana: An International Research Report 147 (1988) pp. 147-52.

Consroe, P. et al., (1986). "Open label evaluation of cannabidiol in dystonic movement disorders" Int'l J Neuroscience 30(4): 277-82.

Consroe, P. et al., "Interaction of cannabidiol and alcohol in humans" Psychopharmacology, 1979. 66(1): p. 45-50.

Constantinescu, C. S. and N. Sarantis (2006). "Long-term open-label treatment with Sativex (R) in patients with multiple sclerosis" Multiple Sclerosis 12: S111-S111 (abstract).

Costa B. et al., (2003) "Cannabidiol is an oral effective therapeutic agent both in acute inflammation and in chronic FCA-induced arthritis" First Eur. Workshop on Cannabinoid Research. Madrid (Spain), p. 62.

Costa B. et al., (2004) "Oral anti-inflammatory activity of cannabidiol, a non-psychoactive constituent of cannabis, in acute carrageenan-induced inflammation in the rat paw" Naunyn-Schmiedebergs Arch Pharmacol 369: 294-299.

Costa B. et al., (2004) "Vanilloid TRPV1 receptor mediates the antihyperalgesic effect of the nonpsychoactive cannabinoid, cannabidiol, in a rat model of acute inflammation" Br J Pharmacol. 143: 247-250.

Costa B et al., (2007) "The non-psychoactive cannabis constituent cannabidiol is an orally effective therapeutic agent in rat chronic inflammatory and neuropathic pain" Eur J Pharmacol 556: 75-83.

Courtenay JS et al., "Immunisation against heterologous type II collagen induces arthritis in mice" 283(5748) Nature 666-68 (1980).

Crippa, J.A.d.S. et al., "Effects of Cannabidiol (CBD) on Regional Cerebral Blood Flow" Neuropsychopharmacology, 2004. 29(2): p. 417-426.

Crombie, et al., "Synthesis of Cannabinoids Carrying omega-Carboxy Substituents: The Cannabidiols, Cannabinol, and $\Delta^1$- and $\Delta^6$-Tetrahydrocannabinols of this Series", J. Chem. Soc. Perkin Trans. vol. 1, pp. 1255-1262 (1988).

Croxford JL (2003) "Therapeutic potential of cannabinoids in CNS disease" CNS Drugs 17: 179-202.

Croxford, J. L. et al., (2008). "Cannabinoid-mediated neuroprotection, not immunosuppression, may be more relevant to multiple sclerosis" J. Neuroimmunology 193(1-2): 120-129.

Cunha, J.M., et al., "Chronic administration of cannabidiol to healthy volunteers and epileptic patients" Pharmacology, 1980. 21(3): p. 175-85.

Dalterio, S. et al., "Early cannabinoid exposure influences neuroendocrine and reproductive functions in male mice: I. Prenatal exposure" Pharmacology, Biochem., and Behavior, 1984. 20(1): p. 107-13.

Dalterio, S. et al., "Early Cannabinoid Exposure Influences Neuroendocrine and Reproductive Functions in Mice II Postnatal Effects" Pharmacology, Biochem., and Behavior, 1984. 20(1): p. 115-123.

Dalterio, S.L. and D.G. deRooij, "Maternal cannabinoid exposure. Effects on spermatogenesis in male offspring" Int J Androl, 1986. 9(4): p. 250-8.

Dalterio, S.L. et al., "Maternal or paternal exposure to cannabinoids affects central neurotransmitter levels and reproductive function in male offspring" Marihuana and Medicine 1999: p. 441-48.

Dalterio, S. et al., (1986). "Perinatal cannabinoid exposure: effects on hepatic cytochrome P-450 and plasma protein levels in male mice" Teratology 33(2): 195-201.

Dalton et al. "Influence of cannabidiol on delta-9-tetrandrocannbinol effects," 19(3) Clinical Pharmacology and Therapeutics 300-09 (1976).

Database CA [Online] Chemical Abstracts Service, Columbus, OH, US; Weiner, et al., "Monomers and Polymers of .Delta.1(6)-Tetrahydrocannabinol and Cannabidiol", European J. Medicinal Chem., vol. 10(1), pp. 79-83 (1975); XP002505688 retrieved from STN Database accession No. 84:59754. 0.

Database CA [Online] Chemical Abstracts Service, Columbus, OH, US; Handrick, et al., "Hashish. 20. Synthesis of (.+-.)-.Delta.1-and .Delta.6-3, 4-cis-cannabidiols and Their Isomerization by Acid Catalysis", J. Organic Chem., vol. 42(15), pp. 2563-8. (1977); XP002505689 retrieved from STN Database accession No. 87:68497.

Database CA [Online] Chemical Abstracts Service, Columbus, OH, US; Knaus, et al., "The Separation, Identification, and Quantitation of Cannabinoids and Their T-Butyldimethylsilyl, Trimethylsilylacetate, and Diethylphosphate Derivatives Using High-Pressure Liquid Chromatography, Gas-Liquid Chromatography, and Mass Spectrometry", J. Chromatographic Science, vol. 14(11), pp. 525-30 (1976); XP002505690 retrieved from STN Database accession No. 86:38182.

Database CA [Online] Chemical Abstracts Service, Columbus, OH, US; Mechoulam, et al., "Hashish. IV. Isolation and Structure of Annabinolic, Cannabidiolic, and Cannabigerolic Acids", Tetrahedron, vol. 21(5), pp. 1223-9 (1965); XP002505691 retrieved from STN Database accession No. 63:16677.

Database CA [Online] Chemical Abstracts Service, Columbus, Ohio, US; Petrzilka, et al., "Synthesis of Hashish Components. Iv", Helvetica Chimica Acta, vol. 52(4), pp. 1102-34 (1969); XP002505692 retrieved from STN Database accession No. 71:21989.

Database CA [Online] Chemical Abstracts Service, Columbus, OH, US; Madinaveitia, et al., "Cannabis Indica. XI. An Examination of the Alkali-Soluble Portion of American-Hemp Resin", J. Chemical Society, pp. 628-30 (1942); XP002505693 retrieved from STN Database accession No. 37:3626.

Database CA [Online] Chemical Abstracts Service, Columbus, OH, US; Hattori, et al., "Gas Chromatography/Negative Ion Chemical Ionization Mass Spectrometry of Cannabinoids in Human Samples", Iyo Masu Kenkyukai Koenshu, vol. 8, pp. 159-60 (1983); XP002505694 retrieved from STN Database accession No. 100:97716.

Davis, et al., "The Emerging Role of Cannabinoid Neuromodulators in Symptom Management", Support Care Cancer vol. 15, pp. 63-71 (2007).

Di Marzo, et al., "Plant, Synthetic, and Endogenous Cannabinoids in Medicine", Annual Review of Med., vol. 57, pp. 553-574 (2006).

Di Marzo, et al., "The Endocannabinoid System and its Therapeutic Exploitation", Nature Reviews, vol. 3, pp. 771-784 (2004).

Dirikoc, S. et al., (2007). "Nonpsychoactive cannabidiol prevents prion accumulation and protects neurons against prion toxicity" J. Neuroscience 27(36): 9537-9544.

de Ridder, D. et al., (2006). "Randomised controlled study of cannabis-based medicine (Sativex (R)) in patients suffering from multiple sclerosis associated detrusor overactivity" Multiple Sclerosis 12: S111-S111.

Deutsch, D. G. et al., (1991). "Potentiation of the inductive effect of phenobarbital on cytochrome P450 mRNAs by cannabidiol" Biochem Pharmacol 42(10): 2048-53.

Dobrosi, et al., "Endocannabinoids Enhance Lipid Synthesis and Apoptosis of Human Sebocytes via Cannabinoid Receptor-2-Mediated Signaling", The FASEB J., vol. 22, pp. 1-11 (Oct. 2008).

Dogrul, et al., "Topical Cannabinoid Antinociception: Synergy With Spinal Sites", Pain vol. 105, pp. 11-16 (2003).

Drysdale and Platt, "Cannabinoids: Mechanisms and Therapeutic Applications in the CNS", Current Medicinal Chem., vol. 10, No. 24, pp. 2719-2732 (2003).

Durst, R. et al., (2007). "Cannabidiol, a nonpsychoactive Cannabis constituent, protects against myocardial ischemic reperfusion injury" Am J Physiol Heart Circ Physiol 293(6): H3602-7.

El-Remessy et al., (2006). "Neuroprotective and blood-retinal barrier-preserving effects of cannabidiol in experimental diabetes" Am J Pathol 168(1): 235-44.

El-Remessy et al., (2003). "Neuroprotective effect of (−)Delta9-tetrahydrocannabinol and cannabidiol in N-methyl-D-aspartate-induced retinal neurotoxicity: involvement of peroxynitrite" Am J Pathol 163(5): 1997-2008.

Esposito, G. et al., (2006). "The marijuana component cannabidiol inhibits beta-amyloid-induced tau protein hyperphosphorylation through Wnt/beta-catenin pathway rescue in PC12 cells" J Mol Med 84(3): 253-8.

Esposito, G. et al., (2006). "Cannabidiol inhibits inducible nitric oxide synthase protein expression and nitric oxide production in beta-amyloid stimulated PC12 neurons through p38 MAP kinase and NF-kappa B involvement" Neuroscience Letters 399(1-2): 91-95.

Esposito, G. et al., (2007). "Cannabidiol in vivo blunts beta-amyloid induced neuroinflammation by suppressing Il-1beta and iNOS expression" Br J Pharmacol 151(8): 1272-9.

Felder, et al., "Cannabinoid Biology: The Search for New Therapeutic Targets", Molecular Interventions, vol. 6, No. 3, pp. 149-161 (2006).

Garcia-Arencibia, M. et al., (2007). "Evaluation of the neuroprotective effect of cannabinoids in a rat model of Parkinson's disease: Importance of antioxidant and cannabinoid receptor-independent properties" Brain Research 1134(1): 162-170.

Gattas, G.J.F. et al., "In vitro cytogenetic effects of cannabidiol on human lymphocyte cultures" Revista Brasileira de Genetica, 1989. 12(3): p. 613-23.

Gerwin N. et al., (2006) "Intraarticular drug delivery in osteoarthritis" Adv Drug Deliv Rev 58: 226- 242.

Gilgun-Sherki, Y. et al., (2003). "The CB1 cannabinoid receptor agonist, HU-210, reduces levodopa-induced rotations in 6-hydroxydopamine-lesioned rats" Pharmacology & Toxicology (Oxford, United Kingdom) 93(2): 66-70.

Gordon and Devinsky, "Alcohol and Marijuana: Effects on Epilepsy and Use by Patients with Epilepsy", Epilepsia, vol. 42, No. 10, pp. 1266-1272 (2001).

Grotenhermen, "Cannabinoids for Therapeutic Use: Designing Systems to Increase Efficacy and Reliability", Amer. J. Drug Delivery, vol. 2(4), pp. 229-240 (2004).

Grotenherman, "Clinical Pharmacokinetics of Cannabinoids", J. Cannabis Therapeutics, vol. 3, No. 1, pp. 3-51 (2003).

Grotenhermen, "Pharmacokinetics and Pharmacodynamics of Cannabinoids", Clinical Pharmacokinetics, vol. 42, No. 4, pp. 327-360 (2003).

Gohda, H. et al., (1990). "In vivo and in vitro metabolism of cannabidiol monomethyl ether and cannabidiol dimethyl ether in the guinea pig: on the formation mechanism of cannabielsoin-type metabolite from cannabidiol" Chem Pharm Bull (Tokyo) 38(6): 1697-701.

Guy, G.W. and M.E. Flint, "A single centre, placebo-controlled, four period, crossover, tolerability study assessing, pharmacodynamic effects, pharmacokinetic characteristics and cognitive profiles of a single dose of three formulations of cannabis based medicine extracts (CBMEs) (GWPD9901), plus a two period tolerability study comparing pharmacodynamic effects and pharmacokinetic characteristics of a single dose of a cannabis based medicine extract given via two administration routes (GWPD9901 EEXT)" J. Cannabis Therapeutics, 2003. 3(3): p. 35-77.

Guy, G. W. and P. J. Robson (2003). "A Phase I, double blind, three-way crossover study to assess the pharmacokinetic profile of cannabis based medicine extract (CBME) administered sublingually in variant cannabinoid ratios in normal healthy male volunteers (GWPK0215)." J. Cannabis Therapeutics 3(4): 121-152.

Guy, G. W. and P. J. Robson (2003). "A Phase I, open label, four-way crossover study to compare the pharmacokinetic profiles of a single dose of 20 mg of a cannabis based medicine extract (Cbme) administered on 3 different areas of the buccal mucosa and to investigate the pharmacokinetics of CBME per oral in healthy male and female volunteers (GWPK0112)"J. Cannabis Therapeutics 3(4): 79-120.

Guy, G. W. and C. G. Stott (2005). "The development of Sativex—a natural cannabis-based medicine" Cannabinoids as Therapeutics: 231-263.

Hamelink, C. et al., (2005). "Comparison of cannabidiol, antioxidants, and diuretics in reversing binge ethanol-induced neurotoxicity" J. Pharmacology and Experimental Therapeutics 314(2): 780-788.

Dana C. Hammell et al, Effect of Cannabidiol Dose in CFA-Induced Mono-Arthritic Rat Model (Apr. 30, 2008) (Abstract).

Hampson, A. J. et al., (1998). "Cannabidiol and (−)Delta-9-tetrahydrocannabinol are neuroprotective antioxidants." Proc. Nat'l Acad. Sci. USA 95: 8268-73.

Hampson, A. J. et al., (2000). "Neuroprotective antioxidants from marijuana." Reactive Oxygen Species: From Radiation to Molecular Biology 899: 274-282.

Hargreaves K. et al., (1988) "A new and sensitive method for measuring thermal nociception in cutaneous hyperalgesia" Pain 32: 77-88.

Harvey D.J. and Brown N.K., "Comparative in vitro metabolism of the cannabinoids" 40(3) Pharmacology, Biochem., and Behavior 533-40 (1991).

Harvey D.J. and Mechoulam R., "Metabolites of cannabidiol identified in human urine" 20(3) Xenobiotica 303-20 (1990).
Hayakawa, K. et al., (2004). "Cannabidiol prevents infarction via the non-CBI cannabinoid receptor mechanism" Neuroreport 15(15): 2381-2385.
Hayakawa, K. et al., (2007). "Delayed treatment with cannabidiol has a cerebroprotective action via a cannabinoid receptor-independent myeloperoxidase-inhibiting mechanism" J. Neurochem. 102(5): 1488-1496.
Hayakawa, K. et al., (2007). "Repeated treatment with cannabidiol but not Delta9-tetrahydrocannabinol has a neuroprotective effect without the development of tolerance" Neuropharmacology 52(4): 1079-87.
Hohmann and Suplita, et al., "Endocannabinoid Mechanisms of Pain Modulation", Amer. Assoc. of Pharmaceutical Scientists J., vol. 8(4), Article 79, pp. E693-E708 (2006).
Hollister, L.E., "Cannabidiol and cannabinol in man" Experientia, 1973. 29(7): p. 825-6.
Huestis, M.A., "Human cannabinoid pharmacokinetics" 4(8) Chem. And Biodiversity 1770-804 (2007).
Huffman, J.W. "Cannabimimetic indoles, pyrroles and indenes," 6(8) Current Medicinal Chem. 705-20 (1999).
Huskey, "Cannabinoids in Cancer Pain Management", J. Pain and Palliative Care Pharmacotherapy, vol. 20(3), pp. 43-46 (2006).
Iskedjian, M. et al., (2007). "Meta-analysis of cannabis based treatments for neuropathic and multiple sclerosis-related pain" Current Medical Research and Opinion 23(1): 17-24.
Iuvone, T. et al., (2004). "Neuroprotective effect of cannabidiol, a non-psychoactive component from *Cannabis sativa*, on beta-amyloid-induced toxicity in PC12 cells." J Neurochem 89(1): 134-41.
Izquierdo, I. et al., Effect of Cannabidiol and of Other Cannabis Sativa Compounds on Hippocampal Seizure Discharges. Psychopharmacologia, 1973. 28(1): p. 95-102.
Izquierdo, I. and Nasello, A.G., "Effects of Cannabidiol and of Diphenylhydantoin on Hippocampus and on Learning" Psychopharmacologia, 1973. 31(2): p. 167-175.
Izquierdo, I. and Tannhauser, M., "Letter: the effect of cannabidiol on maximal electroshock seizures in rats" 25(11) J. Pharmac and Pharmacology 916-17 (1973).
Jaeger, W., et al., (1996). "Inhibition of cyclosporine and tetrahydrocannabinol metabolism by cannabidiol in mouse and human microsomes" Xenobiotica 26(3): 275-84.
Jiang, et al., "Cannabinoids Promote Embryonic and Adult Hippocampus Neurogenesis and Produce Anxiolytic- and Antidepressant-Like Effects", J. Clinical Investigation, vol. 115, No. 11, pp. 3104-3116 (2005).
Jones CA, et al., Health related quality of life outcomes after total hip and knee arthroplasties in a communit based population 27(7) J Rheumatology 1745-52 (2000).
Juckel, G. et al., (2007). "Acute effects of Delta9-tetrahydrocannabinol and standardized cannabis extract on the auditory evoked mismatch negativity" Schizophrenia research 97(1-3): 109-17.
Juntunen, et al., "In-Vitro Corneal Permeation of Cannabinoids and Their Water-Soluble Phosphate Ester Prodrugs", J. Pharmacy and Pharmacology, vol. 57, pp. 1153-1157 (2005).
Juntunen, et al., "Synthesis, in Vitro Evaluation, and Intraocular Pressure Effects of Water-Soluble Prodrugs of Endocannabinoid Noladin Ether," 46(23) J. Medicinal Chem. 5083-86 (2003).
Karsak, et al., "Attenuation of Allergic Contact Dermatitis Through the Endocannabinoid System", Science, vol. 316, pp. 1494-1497 (2007).
Kavia, R. et al., (2006). "Randomised controlled trial of cannabis based medicine (CBM, sativex (R)) to treat detrusor overactivity in multiple sclerosis" Neurourology and Urodynamics 25(6): 622-623.
Kehl, et al., "A Cannabinoid Agonist Differentially Attenuates Deep Tissue Hyperalgesia in Animal Models of Cancer and Inflammatory Muscle Pain", Pain 103, pp. 175-186 (2003).
Kleber, H. D. (2005). "Future advances in addiction treatment" Clinical Neuroscience Research 5(2-4): 201-205.
Klein, "Cannabinoid-Based Drugs as Anti-Inflammatory Therapeutics", Nature Reviews, vol. 5, pp. 400-411 (2005).

Kogan, "Cannabinoids and Cancer", Mini-Reviews in Medicinal Chem., vol. 5, No. 10, pp. 941-952 (2005).
Lambert, et al., "The Endocannabinoid System: Drug Targets, Lead Compounds, and Potential Therapeutic Applications", J. Medicinal Chem., vol. 48, No. 16, pp. 5059-5087 (2005).
Lange and Kruse, "Recent Advances in CB Cannabinoid Receptor Antagonists", Current Opinion in Drug Discovery and Development, vol. 7(4), pp. 498-506 (2004).
Langford R. et al., (2006) "Transdermal fentanyl for improvement of pain and functioning in osteoarthritis" Arthritis Rheum 54(6): 1829-1837.
Lastres-Becker, I. et al., (2005). "Cannabinoids provide neuroprotection against 6-hydroxydopamine toxicity in vivo and in vitro: Relevance to Parkinson's disease" Neurobiology of Disease 19(1-2): 96-107.
Lawrence RC et al., (1998) "Estimates of the prevalence of arthritis and selected musculoskeletal disorders in the United States" Arthritis Rheum 41(5): 778-799.
Lawrence RC et al., "Estimates of the prevalence of arthritis and other rheumatic conditions in the United States. Part II" 58(1) Arthritis Rheum. 26-35 (2008).
Leigh JP et al., (2001) "Estimating the costs of job related arthritis" J Rheumatol 28: 1647-1654.
Lindgren, M., "New Light Shed on Cannabinoid Action (Statistical Data Included)," Citation from Prompt—Predicasts: PMT, World Disease Weekly Plus, Oct. 11, 1999.
List, A. et al., (1977). "The effects of delta9-tetrahydrocannabinol and cannabidiol on the metabolism of gonadal steroids in the rat" Drug metabolism and disposition the biological fate of chemicals 5(3): 268-72.
Leweke, F.M. et al., "Different Effects of Nabilone and Cannabidiol on Binocular Depth Inversion in Man" Pharmacolo. , Biochem., and Behavior, (2000), 66(1): p. 175-181.
Lodzki et al., "Cannabidiol—transdermal delivery and anti-inflammatory effect in a murine model," 93 J. Controlled Release 377-87 (2003).
Lu Y, et al., (2008) "Joint capsule treatment with enkephalin-encoding HSV-1 recombinant vector reduces inflammatory damage and behavioural sequelae in rat CFA monoarthritis" Eur J Neurosci 27:1153-1165.
Lynch, "Preclinical Science Regarding Cannabinoids as Analgesics: An Overview", Pain Res Manage, vol. 10, Suppl. A, pp. 7A-14A (2005).
Malan, et al., (2003) "CB2 cannabinoid receptor agonists: pain relief without psychoactive effects?" Curr. Opin. Pharmacol. 3: 62-67.
Maldonado, et al., "Involvement of the Endocannabinoid System in Drug Addiction", Trends in Neurosciences, vol. 29, No. 4, pp. 225-232 (2006).
Malfait Am et al., (2000) "The nonpsychoactive cannabis constituent cannabidiol is an oral anti-inflammatory therapeutic in murine collagen-induced arthritis" Proc Natl Acad Sci USA 97(17): 9561-9566.
Manzanares, et al., "Interactions Between Cannabinoid and Opioid Receptor Systems in the Mediation of Ethanol Effects", Alcohol & Alcoholism, vol. 40, No. 1, pp. 25-34 (2005).
Marchalant, et al., "Anti-Inflammatory Property of the Cannabinoid Agonist WIN-55212-2 in a Rodent Model of Chronic Brain Inflammation", Neuroscience 144, pp. 1516-1522 (2007).
Martinez, et al., "Dendritic Core—Shell Macromolecules Soluble in Supercritical Carbon Dioxide", Macromolecules, vol. 39, pp. 3978-3979 (2006); see also Martinez, et al., Supporting Information (attached).
Massi, P. et al., (2008). "5-Lipoxygenase and anandamide hydrolase (FAAH) mediate the antitumor activity of cannabidiol, a non-psychoactive cannabinoid" J Neurochem 104(4): 1091-100.
Matsuyama, S.S. and T.K. Fu, "In vivo cytogenetic effects of cannabinoids" J. Clinical Psychopharmacology, 1981. 1(3): p. 135-40.
McAllister et al., "An Aromatic Microdomain at the Cannabinoid CB1 Receptor Constitutes an Agonist/Inverse Agonist Binding Region" 46(24) J Medicinal Chem. 5139-52 (2003).
McArdle, K., et al., (2005). "Cannabidiol: transcriptional and post-transcriptional induction of rat P450s" Toxicology 213(3): 248-249 (Abstract).

McArdle, K. E. et al., (2003). "Cannabidiol (CBD) differentially inhibits Delta(9)-tetrahydrocannabinol (THC) metabolism by human P450s and induces CYP3A23 and CYP2B1/2 in vivo in rat" Toxicology 192(1): 90-91 (Abstract).

McArdle, K. E. et al., (2004). "Differential effects of cannabidiol (CBD) and Delta(9)-tetrahydrocannabinol (THC) on induction of rat cytochrome P450s (CYPs) following in vivo administration" Toxicology 194(3): 237-237 (Abstract).

McKallip, et al., "Cannabidiol-Induced Apoptosis in Human Leukemia Cells: A Novel Role of Cannabidiol in Regulation of $p22^{phox}$ and Nox4 Expression", Molecular Pharmacology, vol. 70, No. 3, pp. 897-908 (2006).

McPartland, J. M. et al., (2007). "Meta-analysis of cannabinoid ligand binding affinity and receptor distribution: interspecies differences" Br J Pharmacol 152(5): 583-93.

McQueen et al., (2004). "Cannabidiol lacks the vanilloid VR1-mediated vasorespiratory effects of capsaicin and anandarnide in anaesthetised rats" European J. Pharmacology 491(2-3): 181-189.

Mechoulam, R. and L. Hanus (2002). "Cannabidiol: an overview of some chemical and pharmacological aspects. Part I: chemical aspects" Chem Phys Lipids 121(1-2): 35-43.

Mechoulam, R. et al., (2002). "Cannabidiol: an overview of some pharmacological aspects" J. Clinical Pharmacology 42(11, Suppl.): 11S-19S.

Melis et al., "Different Mechanisms for Dopaminergic Excitation Induced by Opiates and Cannabinoids in the Rat Midbrain," Progress in Neuro-Psychopharmacology and Biological Psychiatry, vol. 24 (2000), pp. 993-1006.

Michalski, et al., "Cannabinoids Ameliorate Pain and Reduce Disease Pathology in Cerulein-Induced Acute Pancreatitis", Gastroenterology, vol. 132, No. 5, pp. 1968-1978 (2007).

Mishima, K. et al., (2005). "Cannabidiol Prevents Cerebral Infarction Via a Serotonergic 5-Hydroxytryptamine1A Receptor-Dependent Mechanism" Stroke 36(5): 1071-1076.

Muccioli and Lambert, "Current Knowledge on the Antagonists and Inverse Agonists of Cannabinoid Receptors", Current Medicinal Chem., vol. 12, No. 12, pp. 1361-1394 (2005).

Murphy, L.L. et al., "Effects of delta-9-tetrahydrocannabinol, cannabinol and cannabidiol, alone and in combinations, on luteinizing hormone and prolactin release and on hypothalamic neurotransmitters in the male rat" Neuroendocrinology, 1990. 52(4): p. 316-21.

Nahas G. and Trouve R., "Effects and interaction of natural cannabinoids on the isolated heart" 180(2) Proceedings Society for Experimental Biology and Med. 312-16 (1985).

Nalluri, Milligan, Chen, Crooks and Stinchcomb "In vitro release studies on matrix type transdermal drug delivery systems of naltrexone and its acetyl prodrug" Drug Development and Industrial Pharmacy 31(9) (2005), pp. 871-77.

Narimatsu, S. et al., (1990). "Inhibition of hepatic microsomal cytochrome P450 by cannabidiol in adult male rats" Chemical & Pharmaceutical Bulletin 38(5): 1365-8.

Narimatsu, S. et al., (1993). "Suppression of liver microsomal drug-metabolizing enzyme activities in adult female rats pretreated with cannabidiol" Biological & Pharmaceutical Bulletin 16(4): 428-30.

Newhall, W. "Derivatives of (+)-limonene. III. A stereospecific sythesis of cis- and trans-delta-8(9)-p-menthene 1, 2-epoxides" 29 J Organic Chem. 185-86 (1964).

Nurmikko, T. J. et al., (2007). "Sativex successfully treats neuropathic pain characterised by allodynia: A randomised, double-blind, placebo-controlled clinical trial" Pain 133(1-3): 210-220.

Pacher, et al., "The Endocannabinoid System as an Emerging Target of Pharmacotherapy", Pharmacological Reviews, vol. 58, No. 3, pp. 389-462 (2006).

Paria, B.C. et al., "The preimplantation mouse embryo is a target for cannabinoid ligand-receptor signaling" Proc Natl Acad Sci U S A, 1995. 92(21): p. 9460-4.

Patra, P.B. and R.M. Wadsworth, "Quantitative evaluation of spermatogenesis in mice following chronic exposure to cannabinoids" Andrologia, (1991) 23(2): p. 151-6.

Pertwee, "Cannabidiol as a Potential Medicine", Milestones in Drug Therapy: Cannabinoids as Therapeutics, pp. 47-65, R. Mechoulam Ed., Birkhauser Basel (2005).

Pertwee, "The Therapeutic Potential of Drugs That Target Cannabinoid Receptors or Modulate the Tissue Levels or Actions of Endocannabinoids", AAPS J., vol. 7, No. 3, Article 64, pp. E625-E654 (2005).

Pertwee, R. G. (2004). "Pharmacological and therapeutic targets for Delta(9)-tetrahydrocannabinol and cannabidiol" Euphytica 140(1-2): 73-82.

Pertwee, R. G., "The central neuropharmacology of psychotropic cannabinoids" 36(2-3) Pharmacology and Therapeutics 189-261 (1988).

Perez, J. (2006). "Combined cannabinoid therapy via an oromucosal spray" Drugs of today (Barcelona, Spain 1998) 42(8): 495-503.

Perez, J. and M. V. Ribera (2008). "Managing neuropathic pain with Savitex: a review of its pros and ocns" Expert Opinion on Pharmacotherapy 9(7): 1189-1195.

Perez-Reyes, M. et al., "Comparison of the pharmacological activity in man of intravenously administered 9-tetrahydrocannabinol, cannabinol, and cannabidiol" Experientia, 1973. 29(11): p. 1368-9.

Perras, C. (2005). "Sativex for the management of multiple sclerosis symptoms" Issues in emerging health technologies(72): 1-4.

Pertwee, R. G. (2005). "Pharmacological actions of cannabinoids" Handb Exp Pharmacol(168): 1-51.

Pertwee, R. G. et al., (2005). "Evidence that (−)-7-hydroxy-4'-dimethylheptyl-cannabidiol activates a non-CB(1), non-CB(2), non-TRPV1 target in the mouse vas deferens" Neuropharmacology 48(8): 1139-46.

Pillai, et al., "Physicochemical Evaluation, in Vitro Human Skin Diffusion, and Concurrent Biotransformation of 3-O-Alkyl Carbonate Prodrugs of Naltrexone", Pharmaceutical Research, vol. 21, No. 7, pp. 1146-1152 (2004); XP002469233.

Pop et al., "Amino acid esters of dexanabinol (HU-211); prodrugs and analogs" Book of Abstracts, $210^{th}$ ACS National Meeting, Chicago, IL, Aug. 20-24 (Pt. 2): IMEDI-155 (1995).

Pop, E., "Contributions to the chemistry of synthetic cannabinoids." Roumanian Chemical Quarterly III Review vol. 8(1), pp. 19-44 (2001).

Pop et al., "Hydrolytic stability of allylic and phenolic esters of some synthetic cannabinoids: a theoretical (AM1) study." 22 Int'l J Quantum Chem., Quantum Biology Symposium 137-43 (1995).

Reggio, P. H. et al., "Pharmacophores for ligand recognition and activation/inactivation of the cannabinoid receptors" 9(20) Current Pharmaceutical Design 1607-33 (2003).

Reggio et al., "The Bioactive Conformation of Aminoalkylindoles at the Cannabinoid CB1 and CB2 Receptors: Insights Gained from (E)- and (Z)-Naphthylidene Indenes." 41(26) J Medicinal Chem. 5177-87 (1998).

Revuelta, A.V. et al., "Effect of cannabinoids on the turnover rate of acetylcholine in rat hippocampus, striatum and cortex." Naunyn Schmiedebergs Arch Pharmacol, 1978. 304(2): p. 107-10.

Richter A. and Loescher, W. "(+)-Win 55,212-2, a novel cannabinoid receptor agonist, exerts antidystonic effects in mutant dystonic hamsters" 264(3) European J Pharmacology 371-77 (1994).

Rog David, et al., (2005). "Randomized, controlled trial of cannabis-based medicine in central pain in multiple sclerosis" Neurology 65(6): 812-9.

Rog, D. J. et al., (2006). "A Randomized controlled trial of sativex, a cannabis based medicine (CBM), in central neuropathic pain due to multiple sclerosis, followed by an open-label extension" Neurology 66(5): A31-A31 (abstract).

Rog, D. J. et al., (2007). "Long term use of Sativex in multiple sclerosis central pain: Dosing and changes in concomitant analgesia" European J Pain 11(SI:1B6) (abstract).

Rog, D. J. et al., (2007). "Oromucosal delta9-tetrahydrocannabinol/cannabidiol for neuropathic pain associated with multiple sclerosis: an uncontrolled, open-label, 2-year extension trial" Clin Ther 29(9): 2068-79.

Rosenkrantz, H. And Hayden D.W., "Acute and subacute inhalation toxicity of Turkish marihuana, cannabichromene and cannabidiol in rats" 48(3) Toxicology and Applied Pharmacology 375-86 (1979).

Rosenkrantz, H. et al., "Toxicity of short-term administration of cannabinoids to rhesus monkeys" 58(1) Toxicology and Applied Pharmacology 118-31 (1981).

Rukwied, et al., "Cannabinoid Agonists Attenuate Capsaicin-Induced Responses in Human Skin", Pain 102, pp. 283-288 (2003).
Russo, "A Tale of Two Cannabinoids: The Therapeutic Rationale for Combining Tetrahydrocannabinol and Cannabidiol", Medical Hypotheses, pp. 1-13 (2005).
Russo, E. B. (2003). "Safety, tolerability, and efficacy of orally administered cannabinoids in MS" Neurology 60(4): 729-30; author reply 729-30.
Russo, E. B. (2005). "Sativex cannabis based medicine maintains improvements in sleep quality in patients with multiple sclerosis and neuropathic pain" Neurology 64(6): A46-A47.
Russo, E. B. (2008). "Cannabinoids in the management of difficult to treat pain" Therapeutics and Clinical Risk Management 4(1): 245-259.
Russo, E. B. et al., (2007). "Cannabis, pain, and sleep: lessons from therapeutic clinical trials of Sativex, a cannabis-based medicine" Chem. & Biodiversity 4(8): 1729-1743.
Sagredo, O. et al., (2007). "Cannabidiol reduced the striatal atrophy caused 3-nitropropionic acid in vivo by mechanisms independent of the activation of cannabinoid, vanilloid TRPV1 and adenosine A2A receptors" Eur J Neurosci 26(4): 843-51.
Sarantis, N. et al., (2005). "The effect of escape analgesia on pain relief produced by sativex" J. Neurology 252: 154-154 (Abstract).
Selvarajah, D. et al., (2006). "Treatment of painful diabetic neuropathy with Sativex (a cannabis based medicinal product)—results of a radomised placebo controlled trial" Diabetologia 49: 671-672 (Abstract).
Serpell, M. G. and N. Sarantis (2006). "Long-term open-label treatment with Sativex (R), a cannabis based medicine, in neuropathic pain of various aetiologies, and spasticity due to multiple sclerosis" European J. Neurology 13: 239-239 (abstract).
Serpell, M. G. et al., (2005). "The effect of sativex on the Pain Disability Index and the treatment of neuropathic pain" J. Neurology 252: 155-155 (abstract).
Serpell, M. G. et al., (2004). "Sativex (R) in the treatment of pain of neurological origin or symptoms of multiple sclerosis: Interim analysis of a long-term, open-label, safety and tolerability study" European J. Neurology 11: 148-148 (abstract).
Showalter et al., "Evaluation of binding in a transfected cell line expressing a peripheral cannabinoid receptor (CB2): identification of cannabinoid receptor subtype selective ligands" 278(3) J Pharmacology and Experimental Therapeutics 989-99 (1996).
Sibbald, B. (2005). "Conditional okay for cannabis prescription drug" Canadian Medical Assoc. J. 172(13): 1672.
Siemens A.J. and Kalant H. "Metabolism of delta-1-tetrahydrocannabinol by rats tolerant to cannabis" 52(6) Candian J Physiology and Pharmacology 1154-66 (1974).
Siemens A.J. et al., "Effect of cannabis on pentobarbital-induced sleeping time and pentobarbital metabolism in the rat" 23(3) Biochemical Pharmacology 477-88 (1974).
Sluka KA et al., (1993) "Joint inflammation and hyperalgesia are reduced by spinal bicuculline" Neuroreport 5:109-112.
Smith, P. F. (2007). "Symptomatic treatment of multiple sclerosis using cannabinoids: recent advances." Expert Review of Neurotherapeutics 7(9): 1157-1163.
Smiley K.A. et al., "Effects of cannabinoids on the perfused rat heart" 14(4) Research Communications in Chemical Pathology and Pharmacology 659-75 (1976).
Song, Z.H. and Bonner, T.I. "A lysine residue of the cannabinoid receptor is critical for receptor recognition by several agonists but not Win55215-2" 49(5) Molecular Pharmacology 891-96 (1996).
Stinchcomb et al., (2004) "Human skin permeation of delta-8-tetrahydrocannabinol, cannabidiol, and cannabinol" J Pharm Pharmacol 56: 291-297.
Stinchcomb, et al., "Permeation of Buprenorphine and Its 3-Alkyl-Ester Prodrugs Through Human Skin", Pharmaceutical Research, vol. 13, No. 10, pp. 1519-1523 (1996); XP008016388.
Stinchcomb et al., "Straight-chain naltrexone ester prodrugs: diffusion and concurrent esterase biotransformation in human skin" 91(12) J Pharmaceutical Science, pp. 2571-2578 (2002).
Stott, C. G. et al., (2008). "Comparison of pharmacokinetic profiles of inhaled delta-9-tetrahydrocannabinol (THC) from smoked cannabis with Sativex (R) oromucosal spray in humans, implications for possible symptomatic treatment in multiple sclerosis" European J Neurology 15: 365-365 (abstract).
Szallasi et al., "New Perspectives on Enigmatic Vanilloid Receptors," Trends in Neurosciences, vol. 23(10) (2000), pp. 491-497.
Tchilibon, et al., "Synthesis of a Primary Metabolite of Cannabidiol", Organic Letters, vol. 2, No.21, pp. 3301-3303 (2000).
Telek, et al., "Inhibition of Human Hair Follicle Growth by Endo- and Exocannabinoids", The FASEB J., vol. 21, pp. 1-8 (Nov. 2007).
Thomas, A. et al., (2007). "Cannabidiol displays unexpectedly high potency as an antagonist of CB1 and CB2 receptor agonists in vitro" British J of Pharmacology 150: 613-623.
Tomida, I. et al., "Effect of sublingual application of cannabinoids on intraocular pressure: a pilot study" J of Glaucoma, 2006. 15(5): p. 349-53.
Tramposch, A. et al., "Cannabinoid-induced enhancement and depression of cat monosynaptic reflexes" Neuropharmacology, 1981. 20(6): p. 617-21.
Trouve R. and Nahas G. "Cardiac dynamics of the Langendorff perfused heart" 180(2) Proceedings Society for Experimental Biology and Med. 303-11 (1985).
Turkanis, S.A. and R. Karler, "Excitatory and depressant effects of delta 9-tetrahydrocannabinol and cannabidiol on cortical evoked responses in the conscious rat" Psychopharmacology, 1981. 75(3): p. 294-8.
Usami, N. et al., (1999). "A cytochrome P450 enzyme responsible for carbon monoxide formation by cannabidiol in mouse hepatic microsomes" Research Communications in Alcohol and Substances of Abuse 20(1 & 2): 69-77.
Vaddi, H.K., et al., "Human Skin Permeation of Branched-Chain 3-O-Alkyl Ester and Carbonate Prodrugs of Naltrexone" 22(5) Pharmaceutical Research 758-65 (2005).
Valiveti, et al., "In Vitro/In Vivo Correlation Studies for Transdermal $\Delta^8$—THC Development", J. Pharmaceutical Sciences, vol. 93, No. 5, pp. 1154-1164 (2004).
Valiveti, et al., "Intranasal Absorption of $\Delta^9$-tetrahydrocannabinol and WIN55,212-2 Mesylate in Rats", European J. Pharmaceutics and Biopharmaceutics 65, pp. 247-252 (2007).
Valiveti, et al., "Liquid Chromatographic-Mass Spectrometric Qauntitation of $\Delta^9$-tetrahydrocannabinol and Two Metabolites in Pharmacokinetic Study Plasma Samples", J. Chromatography B, vol. 803, pp. 243-248 (2004). ,.
Valiveti, et al., "Transdermal Delivery of the Synthetic Cannabinoid WIN 55,212-2 in Vitro/in Vivo Correlation", Pharmaceutical Research, vol. 21, No. 7. pp. 1137-1145 (2004).
Valiveti, et al., "Transdermal Permeation of WIN 55,212-2 and CP 55,940 in Human Skin in Vitro", International J. Pharmaceutics 278, pp. 173-180 (2004).
Valiveti, et al., "LC-MS method for the estimation of D8-THC and 11-nor-D8-THC-9-COOH in plasma" 38(1) J Pharmaceutical and Biomedical Analysis 112-18 (2005).
Valiveti, et al., "In vivo evaluation of 3-O-alky ester transdermal prodrugs of naltrexone in hairless guinea pigs" 102(5) J Controlled Release 509-20 (2005).
Valiveti, et al., "In vitro/in vivo Correlation of Transdermal Naltrexone Prodrugs in Hairless Guinea Vis" 22(6) Pharmaceutical Research 981-89 (2005).
Vann, R. E. et al., (2008). "Divergent effects of cannabidiol on the discriminative stimulus and place conditioning effects of Delta(9)-tetrahydrocannabinol" Drug and alcohol dependence 94(1-3): 191-8.
Wade, D. T. et al., (2004). "Do cannabis-based medicinal extracts have general or specific effects on symptoms in multiple sclerosis? A double-blind, randomized, placebo-controlled study on 160 patients" Multiple Sclerosis 10(4): 434-441.
Wade, D. T. et al., (2006). "Long-term use of a cannabis-based medicine in the treatment of spasticity and other symptoms in multiple sclerosis" Multiple sclerosis (Houndmills, Basingstoke, England) 12(5): 639-45.
Watanabe, K. et al., (1987). "Self-catalyzed inactivation of cytochrome P-450 during microsomal metabolism of cannabidiol" Biochemical Pharmacolo• 36(20): 3371-7.
Watanabe, K., et al., (1986). "Effects of two cannabinoids on hepatic microsomal cytochrome P-450" J Pharmacobio-Dynamics 9(1): 39-45.

Watanabe, K. et al., (1988). "Formation of similar species to carbon monoxide during hepatic microsomal metabolism of cannabidiol on the basis of spectral interaction with cytochrome P-450" Biochemical Pharmacology 37(24): 4719-26.

Williamson, et al., "Cannabinoids in Clinical Practice", Drugs, vol. 60, No. 6, pp. 1303-1314 (2000).

Wright, S. et al., (2006). "The use of a cannabis-based medicine (Sativex) in the treatment of pain caused by rheumatoid arthritis" Rheumatology (Oxford, England) 45(6): 781; author reply 781.

Yamamoto, I. et al., (2003). "Pharmacology and Toxicology of Major Constituents of Marijuana-On the Metabolic Activation of Cannabinoids and Its Mechanism." J Toxicology, Toxin Reviews 22(4): 577-589.

Yamamoto, I. et al, "Recent advances in the metabolism of cannabinoids" 27(8) Int'l J Biochem. and Cell Biology 741-46 (1995).

Yoo, S.D. et al., "Mammary excretion of cannabidiol in rabbits after intravenous administration" J Pharm Pharmacol, 1994. 46(11): p. 926-8.

Zhang L et al., (2004) "Restoration of spontaneous exploratory behaviors with an intraecal NMDA receptor antagonist or a PKC inhibitor in rats with acute pancreatitis" Pharmacol Biochem Behav 77: 145-153.

Zimmer A et al., (1999) "Increased mortality, hypoactivity, and hypoalgesia in cannabinoid CB1 receptor knockout mice" Proc Natl Acad Sci USA 96: 5780-5785.

Zimmerman, A.M. et al., "Effects of cannabinoids on sperm morphology" Pharmacology, (1979). 18(3): p. 143-8.

Zimmerman A.M. and Raj A.Y., "Influence of cannabinoids on somatic cells in-vivo" 21(4) Pharmacology 277-87 (1980).

Zuardi, A.W., et al., "Effects of ipsapirone and cannabidiol on human experimental anxiety" J of Psychopharmacology (London, United Kingdom), 1993. 7(1): p. 82-8.

Zuardi, A.W. et al., "Effect of cannabidiol on plasma prolactin, growth hormone and cortisol in human volunteers" Brazilian J of Medical and Biological Research, 1993. 26(2): p. 213-17.

Zuardi, A.W. et al., "Cannabidiol monotherapy for treatment-resistant schizophrenia" J Psychopharmacology (London, United Kingdom), 2006. 20(5): p. 683-686.

Zuardi, A.W. et al., "Action of cannabidiol on the anxiety and other effects produced by delta-9-THC in normal subjects" Psychopharmacology (Berlin, Germany), 1982. 76(3): p. 245-50.

Zuardi, A.W., et al., "Cannabidiol for the treatment of psychosis in Parkinson's disease" European Neuropsychopharmacology, 2008. 18: p. S417-S418.

Zuardi, A., et al., "Cannabidiol was ineffective for manic episode of bipolar affective disorder" J Psychopharmacol, 2008.

Thong, et al, "Percutaneous Penetration Enhancers: An Overview." 20 Skin Pharmacology & Physiology 272-82 (2007).

Auxillium Pharmaceutical, Inc. Citizen's Petition Decision, Aug. 26, 2009.

Fabin B, et al., "Localization of Lipophilic Molecules Penetrating Rat Skin in Vivo by Quantitative Autoradiography", International Journal of Pharmaceutics, Elseveir BV, vol. 74, No. 1, pp. 59-65 (1991); XP025544203 ISSN: 0378-5173.

Extended European Search Report for European Pat. Appl. No. 06 784 961.2 (PCT/US2006/023387), Jul. 23, 2009.

Ansel et al., Pharmaceutical Dosage Forms and Drug Delivery Systems, 7th ed., Chapter 9, pp. 244-245 (1999).

Catz, et al., "Transdermal delivery of levonorgestrel. VIII. Effect of enhancers on rat skin, hairless mouse skin, hairless guinea pig skin, and human skin," Int'l Journal of Pharmaceutics, vol. 58, pp. 93-102 (1990).

Gattefossé, Lipid Excipients for Topical Drug Delivery.

Gattefossé, Transcutol®—Improving drug delivery in topical products.

Pathan, et al., "Comparison of the Effect of Essential Oils on the Permeation of Diclofenac Diethylamine Through Various Barriers," Acta Pharmaceutica Sciencia, vol. 50(3), pp. 219-228 (2008).

Shakeel, et al., "Nanoemulsions as Vehicles for Transdermal Delivery of Aceclofenac," AAPS PharmSciTech, vol. 8 (4), pp. E1-E9 (2007).

Related U.S. Appl. No. 13/271,338 dated Mar. 27, 2012.

Mendizabal et al., "Cannabinoid system as a potential target for drug development in the treatment of cardiovascular disease", Current Vascular Pharmacology, 2003, vol. 1, pp. 301-313.

Büyüktimkin, et al., "Synthesis and Enhancing Effect of Dodecyl 2-(N,N-Dimethylamino)propionate on the Transepidermal Delivery of Indomethacin, Clonidine, and Hydrocortisone." Pharmaceutical Research; vol. 10(11), pp. 1632-1637 (1993).

Choi, et al., "Formulation and Evaluation of Ketorolac Transdermal Systems," Drug Delivery, vol. 14, pp. 69-74 (2007).

Gennaro, Alfonso, Remington: The Science and Practice of Pharmacy, 20th ed., pp. 842-843 (2000).

Givak et al., "Effect of vehicles and penetration enhancers on the in vitro percutaneous absorption of tenoxicam through hairless mouse skin," International Journal of Pharmaceutics, vol. 236, pp. 57-64 (2002).

Harrison, et al., "The Relative Effect of Azone® and Transcutal® on Permeant Diffusivity and Solubility in Human Stratum corneum," Pharmaceutical Research, vol. 13(4), pp. 542-546 (1996).

Helton, et al., "Pharmaookinetic profiles in rats after intravenous oral, or dermal administration of dapsone," Drug Metabolism and Disposition, vol. 28(8), pp. 925-929 (2000).

Møllgaard, et al., "Permeation of estradiol through the skin-effect of vehicles," International Journal of Pharmaceutics, vol. 15, pp. 185-197 (1983).

Puglia, et al., "Evaluation of in vitro percutaneous absorption of lorazepam and clonazeparn from hydro-alcoholic gel formulations," International Journal of Pharmaceutics, vol. 228, pp. 79-87 (2001).

Sintov, et al., "Cutaneous biotransformation of N-(4-bromobenzoyl)-S,S-dimethylirninosulfurane and its product, 4-bromoberizamide, leading to percutaneous penetration enhancement of drugs: Initial evidence using hydrocortisone." Journal of Controlled Release, vol. 133, pp. 44-51 (2009).

Walters, Kenneth, "Penetration Enhancers and Their Use in Transdermal Therapeutic Systems." Transderal Drug Delivery Developmental Issues arid Research Initiatives, Marcel Dekker, Inc, pp. 197-246, 1989.

Williams, S. J. et al., "Brochodilator Effect of Delta-1-Tetrahydrocannabinol Administered by Aerosol to Asthmatic Patients," Thorax, vol. 31, 1976, pp. 720-723.

Noyes, R. et al., "Analgesic Effect of Delta-9-Tetrahydrocannabinol," Journal of Clinical Pharmacology, Feb.-Mar. 1975, pp. 139-143.

Noyes, R. et al., "The Analgesic Properties of Delta-9-Tetrahydrocannabinol and Codeine," Clinical Pharmacology and Therapeutics, vol. 18, No. 1, Mar. 29, 1975, pp. 86-89.

Sallan, S. F. et al., "Antiemetic Effect of Delta-0-Tetrahydrocannabinol in Patients Receiving Cancer Chemotherapy," New England Journal of Medicine, vol. 293, No. 16, Oct. 16, 1975, pp. 795-797.

Hansch, C. et al., "Aromatic Substituent Constants for Structure—Activity Correlations," Journal of Medicinal Chemistry, vol. 16, No. 11, 1973, pp. 1207-1213.

Bondi, A. "van der Waals Volumes and Radii," The Journal of Physical Chemistry, vol. 68, No. 3, Mar. 16, 1964, pp. 441-451.

Lowry, D. H. et al., "Protein Measurment with the Folin Phenol Reagent," From the Department of Pharmacology, Washington University School of Medicine, St. Louis, Missouri, May 28, 1951, pp. 265-275.

Glasstone, SL. Textbook of Physical Chemistry, $2^{nd}$ Edition, D. Van Nostrand, NY, 1946, pp. 529-530.

Flynn, G.I. "Cutaneous and Transdermal Delivery: Process and Systems Delivery," Modern Pharmaceutics, Third Edition, pp. 239-298, 2002.

Hoffman, D. et al., "On the Carcinogenicity of Marijuana Smoke," Recent Advances in Phytochemistry, vol. 9, pp. 63-81, 1975.

NCADI: NIH's Workshop on the Medical Utility of Marijuana, http://www.health.org/medmarj.htm, 1998, pp. 1-33.

"Therapeutic Usies of Cannabis," British Medical Association, Harwood Academic Publishers, 1997, pp. 10, 11, 26-45, 75-81.

Touitou, E. et al., "Transdermal Delivery of Tetrahydrocannabinol." International Journal of Pharmaceutics, vol. 43, 1988, pp. 9-15.

* cited by examiner

TRANSDERMAL DELIVERY OF CANNABIDIOL

BACKGROUND OF THE INVENTION

1. Technical Field

The present invention generally relates to the transdermal delivery of cannabinoids. More particularly, the present invention relates to a method and mode of transdermally delivering cannabinoids to treat various illnesses and/or symptoms.

2. Background Art

The use of cannabinoids to treat medical illnesses is of great interest to the medical community. Specifically, illnesses such as AIDS and cancer are often accompanied with a lack of appetite. Moreover, patients receiving cancer chemotherapy often experience nausea and vomiting side effects. Chronic pain (especially neuropathic pain), malignant tumors, spasticity (in multiple sclerosis and spinal cord injury), and or dystonia are additional therapeutic targets for cannabinoid therapy. The capability to control or eliminate these problems would greatly increase the quality of life for many patients.

Heretofore, attempts have been made at administering the cannabinoid $\Delta^9$-THC (Dronabinol) orally, in the form of a capsule. However, severely nauseated patients are often not able to retain the capsule in their stomachs long enough for the drug to take effect. This problem is compounded by the fact that four to six doses of the capsule must be taken around chemotherapy. Another issue with capsules, as well as smoked marijuana, is that patients absorb the drug relatively rapidly (as compared to controlled drug delivery rates that a patch produces) and receive high drug concentrations in their body. These high drug concentrations, or peak levels, are often associated with serious psychoactive and other central nervous system side effects.

In view of the above, there is a long felt need in the art for $\Delta^9$-THC and other cannabinoids to be delivered transdermally (across the skin). Preferably, such cannabinoids will be delivered by patch, bandage, topical formulation or the like and release the appropriate dose of cannabinoids over time. There is also a need to transdermally deliver cannabinoids other than $\Delta^9$-THC and $\Delta^8$-THC to treat various illnesses and/or symptoms.

SUMMARY OF THE INVENTION

The present invention overcomes the problems associated with existing drug delivery systems by delivering cannabinoids transdermally. Preferably, the cannabinoids are delivered via an occlusive body (i.e., a patch) to alleviate harmful side effects and avoid gastrointestinal (first-pass) metabolism of the drug by the patient.

A first aspect of the invention provides a method for relieving symptoms associated with illness or associated with the treatment of illness in a mammalian subject, comprising the steps of selecting at least one cannabinoid from the group consisting of cannabinol, cannabidiol, nabilone, levonantradol, (−)-HU-210, (+)-HU-210, 11-hydroxy-$\Delta^9$-THC, $\Delta^8$-THC-11-oic acid, CP 55,940, and R(+)-WIN 55,212-2, selecting at least one permeation enhancer from the group consisting of propylene glycol monolaurate, diethylene glycol monoethyl ether, an oleoyl macrogolglyceride, a caprylocaproyl macrogolglyceride, and an oleyl alcohol, and delivering the selected cannabinoid and permeation enhancer transdermally to treat an illness.

A second aspect of the invention provides an occlusive body for the delivery of cannabinoids, comprising an impermeable backing, a rate-controlling microporous membrane, said backing and membrane defining a cavity therebetween, a cannabinoid disposed within the cavity, a permeation enhancer disposed within the cavity, and a viscous flowable gel confined between the backing and the membrane within the cavity for immobilizing the cannabinoid and the permeation enhancer.

A third aspect of the invention provides a method for increasing the concentration of cannabinoids or cannabinoid metabolites in a subject, comprising contacting the subject's skin with a compound selected from the group consisting of cannabinol, cannabidiol, nabilone, levonantradol, (−)-HU-210, (+)-HU-210, 11-hydroxy-$\Delta^9$-THC, $\Delta^8$-THC-11-oic acid, CP 55,940, and R(+)-WIN 55,212-2 and contacting the subject's skin with a permeation enhancer selected from the group consisting of propylene glycol monolaurate, diethylene glycol monoethyl ether, an oleoyl macrogolglyceride, a caprylocaproyl macrogolglyceride, and an oleyl alcohol.

The preferred embodiment of the present invention is designed to solve the problems herein described and other problems not discussed, which are discoverable by a skilled artisan.

DETAILED DESCRIPTION

Figure 1:
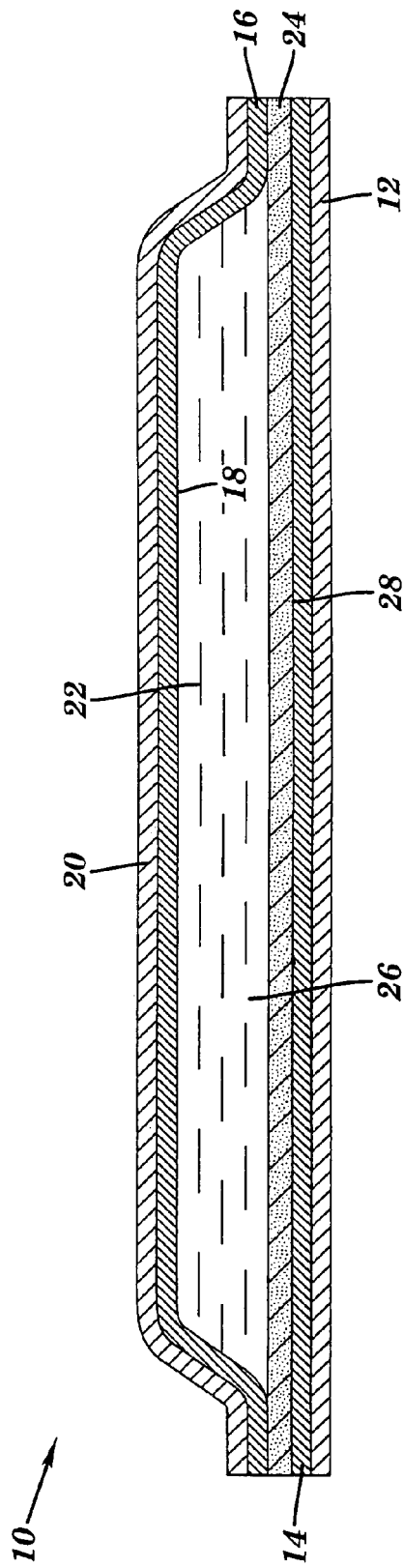
FIG. 1 is a cross-sectional view of an occlusive body in accordance with the present invention.

The present invention relates to a method for relieving symptoms associated with illness or discomfort associated with the treatment of illness in a subject.

Subjects who can benefit from the method of the present invention include, for example, mammals, such as humans, particularly humans requiring relief from chronic pain, such as neuropathic pain.

The method of the present invention can be used to relieve the symptoms of a variety of diseases, conditions, syndromes, disorders, and other forms of illness. For example, as explained above, patients suffering from illnesses, such as cancer and AIDS, often experience symptoms, such as lack of appetite, which can be relieved with the method of the present invention. Patients suffering from neuropathy experience chronic pain and other symptoms which can be relieved with the method of the present invention. Patients suffering from multiple sclerosis or spinal cord injury experience spasticity and other symptoms that can be relieved with the method of the present invention. The methods of the present invention can also be used to relieve symptoms associated with dystonia and malignant tumors. The methods of the present invention can also be used to relieve symptoms of stroke, head injuries, neurodegenerative disorders, and other conditions, diseases, and disorders associated with the N-methyl-D-aspartate receptor. Still other diseases and disorders that the present invention may prove useful in treating include Huntington's disease, arthritis, nervous-tissue inflammation, vascular inflammation, inflammatory bowel disease, and other inflammation-related conditions. The mechanism by which symptoms are relieved is not particularly critical to the practice of the present invention. Illustratively, symptoms can be relieved by directly treating the underlying illness or by blocking the biological pathways by which the illness produces the symptoms.

Moreover, the method of the present invention can be used to relieve discomfort associated with the treatment of illness. Illustratively, the method of the present invention can be used to relieve nausea, vomiting, and/or other discomforts associated with chemotherapy and other treatment regimens used to treat cancer and other illnesses.

"Relieve," as used herein, is meant to include complete elimination as well as any clinically or quantitatively measurable reduction in the subject's symptoms and/or discomfort.

The method of the present invention involves providing a cannabinoid composition. The cannabinoid composition includes at least one cannabinoid selected from the group consisting of $\Delta^9$-THC, cannabinol, cannabidiol, nabilone, levonantradol, (−)-HU-210, (+)-HU-210, 11-hydroxy-$\Delta^9$-THC, $\Delta^8$-THC-11-oic acid, CP 55,940, and R(+)-WIN 55,212-2.

"Cannabinoid," as used herein, is meant to include compounds which interact with the cannabinoid receptor and various cannabinoid mimetics, such as certain tetrahydropyran analogs (e.g., $\Delta^9$-tetrahydrocannabinol, $\Delta^8$-tetrahydrocannabinol, 6,6,9-trimethyl-3-pentyl-6H-dibenzo[b,d]pyran-1-ol, 3-(1,1-dimethylheptyl)-6,6a,7,8, 10,10a-hexahydro-1-hydroxy-6,6-dimethyl-9H-dibenzo[b,d]pyran-9-one, (−)-(3S,4S)-7-hydroxy-$\Delta^6$-tetrahydrocannabinol-1,1-dimethylheptyl, (+)-(3S,4S)-7-hydroxy-$\Delta^6$-tetrahydrocannabinol-1,1-dimethylheptyl, 11-hydroxy-$\Delta^9$-tetrahydrocannabinol, and $\Delta^8$-tetrahydrocannabinol-11-oic acid)); certain piperidine analogs (e.g., (−)-(6S,6aR,9R, 10aR)-5,6,6a,7,8,9,10,10a-octahydro-6-methyl-3-[(R)-1-methyl-4-phenylbutoxy]-1,9-phenanthridinediol 1-acetate)), certain aminoalkylindole analogs (e.g., (R)-(+)-[2,3-dihydro-5-methyl-3-(4-morpholinylmethyl)-pyrrolo[1,2,3-de]-1,4-benzoxazin-6-yl]-1-naphthalenyl-methanone), certain open pyran ring analogs (e.g., 2-[3-methyl-6-(1-methylethenyl)-2-cyclohexen-1-yl]-5-pentyl-1,3-benzenediol and 4-(1,1-dimethylheptyl)-2,3'-dihydroxy-6'alpha-(3-hydroxypropyl)-1', 2',3',4',5',6'-hexahydrobiphenyl), as well as their pharmaceutically acceptable salts, solvates, metabolites (e.g., cutaneous metabolites), and metabolic precursors. Further examples of "cannabinoids" include those compounds described in the references cited below.

"$\Delta^9$-THC," as used herein, is meant to refer to $\Delta^9$-tetrahydrocannabinol as well as to its pharmaceutically acceptable salts, solvates, metabolites (e.g., cutaneous metabolites), and metabolic precursors. $\Delta^9$-tetrahydrocannabinol is marketed under the generic name "dronabinol."

"Cannabinol," as used herein, is meant to refer to 6,6,9-trimethyl-3-pentyl-6H-dibenzo[b,d]pyran-1-ol as well as to pharmaceutically acceptable salts, solvates, metabolites (e.g., cutaneous metabolites), and metabolic precursors of 6,6,9-trimethyl-3-pentyl-6H-dibenzo[b,d]pyran-1-ol. The synthesis of 6,6,9-trimethyl-3-pentyl-6H-dibenzo[b,d]pyran-1-ol is described in, for example, Novak et al., *Tetrahedron Letters*, 23:253 (1982), which is hereby incorporated by reference.

"Cannabidiol," as used herein, is meant to refer to 2-[3-methyl-6-(1-methylethenyl)-2-cyclohexen-1-yl]-5-pentyl-1,3-benzenediol as well as to pharmaceutically acceptable salts, solvates, metabolites (e.g., cutaneous metabolites), and metabolic precursors of 2-[3-methyl-6-(1-methylethenyl)-2-cyclohexen-1-yl]-5-pentyl-1,3-benzenediol. The synthesis of 2-[3-methyl-6-(1-methylethenyl)-2-cyclohexen-1-yl]-5-pentyl-1,3-benzenediol is described, for example, in Petilka et al., *Helv. Chim. Acta,* 52:1102 (1969) and in Mechoulam et al., *J. Am. Chem. Soc.,* 87:3273 (1965), which are hereby incorporated by reference.

"Nabilone," as used herein, is meant to refer to 3-(1,1-dimethylheptyl)-6,6a,7,8,10,10a-hexahydro-1-hydroxy-6,6-dimethyl-9H-dibenzo[b,d]pyran-9-one as well as to pharmaceutically acceptable salts, solvates, metabolites (e.g., cutaneous metabolites), and metabolic precursors of 3-(1,1-dimethylheptyl)-6,6a,7,8, 10,10a-hexahydro-1-hydroxy-6,6-dimethyl-9H-dibenzo[b,d]pyran-9-one. 3-(1,1-dimethylheptyl)-6,6a,7,8,10,10a-hexahydro-1-hydroxy-6,6-dimethyl-9H-dibenzo[b,d]pyran-9-one is approved for use in the United Kingdom for treating nausea and vomiting associated with chemotherapy, and its preparation is described, for example, in U.S. Pat. No. 3,968,125 to Archer, which is hereby incorporated by reference.

"Levonantradol," as used herein, is meant to refer to (−)-(6S,6aR,9R,10aR)-5,6,6a,7,8,9,10,10a-octahydro-6-methyl-3-[(R)-1-methyl-4-phenylbutoxy]-1,9-phenanthridinediol 1-acetate, as well as to pharmaceutically acceptable salts, solvates, metabolites (e.g., cutaneous metabolites), and metabolic precursors of (−)-(6S,6aR,9R, OaR)-5,6,6a,7,8,9, 10,10a-octahydro-6-methyl-3-[(R)-1-methyl-4-phenylbutoxy]-1,9-phenanthridinediol 1-acetate. (−)-(6S,6aR,9R, 10aR)-5,6,6a,7,8,9,10,10a-octahydro-6-methyl-3-[(R)-1-methyl-4-phenylbutoxy]-1,9-phenanthridinediol 1-acetate is particularly useful in pain control, and its synthesis is described in Belgian Pat. No. 854,655, which is hereby incorporated by reference; in U.S. Pat. Nos. 4,206,225, 4,232,018, and 4,260,764, each to Johnson, which are hereby incorporated by reference; in U.S. Pat. No. 4,235,913 to Johnson et al., which is hereby incorporated by reference; in U.S. Pat. No. 4,243,674 to Bindra, which is hereby incorporated by reference; and in U.S. Pat. Nos. 4,263,438, 4,270,005, and 4,283,569, each to Althuis et al., which are hereby incorporated by reference.

"(−)-HU-210," as used herein, is meant to refer to (−)-(3S, 4S)-7-hydroxy-$\Delta^6$-tetrahydrocannabinol-1,1-dimethylheptyl as well as to pharmaceutically acceptable salts, solvates, metabolites (e.g., cutaneous metabolites), and metabolic precursors of (−)-(3S,4S)-7-hydroxy-$\Delta^6$-tetrahydrocannabinol-1,1-dimethylheptyl. (−)-(3S,4S)-7-hydroxy-$\Delta^6$-tetrahydrocannabinol-1,1-dimethylheptyl is particularly useful in pain control, and its preparation is described in U.S. Pat. Nos. 4,876,276 and 5,521,215, each to Mechoulam et al., which are hereby incorporated by reference.

"(+)-HU-210," as used herein, is meant to refer to (+)-(3S, 4S)-7-hydroxy-$\Delta^6$-tetrahydrocannabinol-1,1-dimethylheptyl as well as to pharmaceutically acceptable salts, solvates, metabolites (e.g., cutaneous metabolites), and metabolic precursors of (+)-(3S,4S)-7-hydroxy-$\Delta^6$-tetrahydrocannabinol-1,1-dimethylheptyl. (+)-(3S,4S)-7-hydroxy-$\Delta^9$-tetrahydrocannabinol-1,1-dimethylheptyl is sometimes referred to as HU-211 and/or dexanabinol; it is an antagonist of the N-methyl-D-aspartate receptor; and its preparation is described in U.S. Pat. Nos. 4,876,276 and 5,521,215, each to Mechoulam et al., which are hereby incorporated by reference.

"11-hydroxy-$\Delta^9$-THC," as used herein is meant to refer to 11-hydroxy-$\Delta^9$-tetrahydrocannabinol as well as to its pharmaceutically acceptable salts, solvates, metabolites (e.g., cutaneous metabolites), and metabolic precursors. 11-hydroxy-$\Delta^9$-tetrahydrocannabinol is a more hydrophilic, psychoactive metabolite of $\Delta^9$-tetrahydrocannabinol, and its laboratory synthesis has been described in Siegel et al., *J. Org. Chem.*, 54:5428 (1989), which is hereby incorporated by reference.

"$\Delta^8$-THC-11-oic acid," as used herein, is meant to refer to $\Delta^8$-tetrahydrocannabinol-11-oic acid, as well as to its pharmaceutically acceptable salts, solvates, metabolites (e.g., cutaneous metabolites), and metabolic precursors. $\Delta^8$-tetrahydrocannabinol-11-oic acid is a naturally occurring derivative of 6a,7,10,10a-tetrahydro-6,6,9-trimethyl-3-pentyl-6H-dibenzo[b,d]pyran-1-ol (which is a minor component of *Cannabis sativa*) and is produced from 6a,7, 10,10a-tetrahydro-6,6,9-trimethyl-3-pentyl-6H-dibenzo[b,d]pyran-1-ol via a series of biotransformations mediated primarily by mammalian liver enzymes. A8-tetrahydrocannabinol-11-oic acid can also be produced synthetically by reference to the synthetic schemes set forth in U.S. Pat. No. 6,162,829 to Burstein, which is hereby incorporated by reference. $\Delta^8$-tetrahydrocannabin-ol-11-oic acid is more hydrophilic than 6a,7,10,10a-tetrahydro-6,6,9-trimethyl-3-pentyl-6H-dibenzo[b,d]pyran-1-ol, and it has analgesic activity.

"CP 55,940," as used herein, refers to 4-(1,1-dimethylheptyl)-2,3'-dihydroxy-6'alpha-(3-hydroxypropyl)-1',2',3',4',5', 6'-hexahydrobiphenyl, as well as to its pharmaceutically acceptable salts, solvates, metabolites (e.g., cutaneous metabolites), and metabolic precursors. 4-(1,1-dimethylheptyl)-2,3'-dihydroxy-6'alpha-(3-hydroxypropyl)-1',2',3',4',5', 6'-hexahydrobiphenyl is sometimes referred to as (−)-cis-3-[2-Hydroxy-4-(1,1-dimethylheptyl)phenyl]-trans-4-(3-hydroxypropyl) cyclohexanol, and it is commercially available from Tocris Cookson, Inc., Ellisville, Mo. Its preparation has been described in U.S. Pat. No. 4,371,720 to Johnson et al. and U.S. Pat. No. 4,663,474 to Urban, which are hereby incorporated by reference.

"R(+)-WIN 55,212-2," as used herein, refers to (R)-(+)-[2, 3-dihydro-5-methyl-3-(4-morpholinylmethyl)-pyrrolo[1,2, 3-de]-1,4-benzoxazin-6-yl]-1-naphthalenyl-methanone, as well as to its pharmaceutically acceptable salts, solvates, metabolites (e.g., cutaneous metabolites), and metabolic precursors. (R)-(+)-[2,3-dihydro-5-methyl-3-(4-morpholinylmethyl)-pyrrolo[1,2,3-de]-1,4-benzoxazin-6-yl]-1-naphthalenyl-methanone (in its mesylate form) is commercially available, for example, from Tocris Cookson, Inc., Ellisville, Mo., and from Research Biochemicals International, Natick, Mass.

The cannabinoid composition can further include one or more additional cannabinoids. The one or more additional cannabinoids can be selected from the aforementioned list of cannabinoids or it (they) can be selected from cannabinoids which are not contained in the aforementioned list, such as $\Delta^8$-THC, high affinity cannabinoid receptor agonists (other than R(+)-WIN 55,212-2 and CP 55,940), and the like. Illustratively, the cannabinoid composition can include two or more cannabinoids, each being selected from the group consisting of $\Delta^9$-THC, cannabinol, cannabidiol, nabilone, levonantradol, (−)-HU-210, (+)-HU-210, 11-hydroxy-$\Delta^9$-THC, $\Delta^8$-THC-11-oic acid, CP 55,940, and R(+)-WIN 55,212-2.

"Metabolic precursors" of cannabinoids, as used herein, are meant to include prodrugs and other materials that are metabolized in the subject's body (e.g., cutaneously or systemically or both) to a cannabinoid or an active cannabinoid mimetic. Suitable metabolic precursors include those that are less lipophilic (i.e., more water soluble) relative to the cannabinoid into which they are metabolized. Examples of such metabolic precursors include those described in, for example, U.S. Pat. No. 5,847,128 to Martin et al., which is hereby incorporated by reference.

"Metabolites" of cannabinoids, as used herein, are meant to include compounds which are produced by the metabolic processes (e.g., cutaneous metabolic processes and/or systemic metabolic processes) of the subject's body. Suitable metabolites can be identified, for example, by studying the kinetics of drug enzymatic metabolism in skin homogenates. Illustratively, skin homogenates can be prepared from 250-μm dermatomed fresh healthy abdominal plastic surgery samples. The skin is homogenized (e.g., using a Polytron tissue homogenizer and ground glass homogenizer fitted with a glass pestle) in 4-(2-hydroxyethyl)-1-piperazineethanesulfonic acid ("HEPES")-buffered Hanks' balanced salt solution. Whole homogenates can be used for these studies or, if significant mitochondrial or nuclear metabolism is found not to occur (e.g., by comparing the degree of metabolism in the supernatant to the degree of metabolism in the whole homogenate), the studies can be carried out on only the supernatant fraction. The drug (solubilized in, for example, buffer, ethanol, dimethylsulfoxide, or combinations thereof) is then incubated with the homogenate (or supernatant) along with NADPH (or a generating system), NADH, $MgCl_2$, and bovine serum albumin. The total volume of ethanol in the reaction mixture should be small (e.g., under 2%) to help minimize ethanol's detrimental effects on the enzymes. After incubating for a period of time, the reaction is terminated with 15% trichloroacetic acid, and the drug and its metabolites are obtained by solid-phase extraction. The metabolite or metabolites formed can then be identified and assayed by any suitable method (e.g., HPLC).

As one skilled in the art will recognize, optimization of the method of the present invention will involve consideration of a variety of factors in selecting the cannabinoid to be used. One such factor is skin permeability. Several physicochemical factors influence the ability of cannabinoids to penetrate the skin. These include the cannabinoid's molecular weight, its molecular volume, its lipophilicity, its hydrogen bonding potentials, its polarity, etc.

As indicated above, once the cannabinoid composition is provided, the cannabinoid is delivered transdermally to the subject, for example, by iontophoresis; by phonophoresis; by using microneedle technologies; by applying the cannabinoid as a topical cream, salve, ointment, or other topical formulation; and/or by using delivery devices such as bandages, patches, and/or the like. Generally speaking, transdermal delivery involves contacting the cannabinoid composition with the subject's skin under conditions effective for at least one of the provided cannabinoids to penetrate the skin.

Illustratively, the cannabinoid composition can be formulated as a topical cream, salve, or ointment. The topical formulations can include inert diluents and carriers as well as other conventional excipients, such as wetting agents, preservatives, and suspending and dispersing agents. In addition to the above, generally non-active components, topical formulations containing the cannabinoid composition can further include other active materials, particularly, active materials which have been identified as useful in the treatment of pain, discomfort, or other conditions associated with a subject's illness and which can usefully be delivered transdermally to the subject. For instance, such other active materials can include analgesics, such as opiates and other analgesic active materials which operate on non-cannabinoid receptors. Where, for example, opiates are included, transdermally deliverable opiates are particularly preferred. One example of a transdermally deliverable opiate is fentanyl. The topical formulation can be applied directly to the skin and then optionally covered (e.g., with a bandage of gauze) to minimize the likelihood of its being disturbed. Alternatively, the topical formulation can be coated on the surface of a bandage, gauze, etc., and the bandage, gauze, etc. can then be applied to the skin of the subject such that the topical formulation is in direct contact with the subject's skin.

Alternatively, the cannabinoid can be delivered transdermally to the subject by formulating the cannabinoid composition into a bandage, pad, or other type of patch which can be applied to the subject's skin.

Illustratively, matrix-type transdermal patches, in which the selected cannabinoid is disposed in an adhesive matrix, can be employed. The matrix-type transdermal patch can further include other cannabinoids and other active materials (e.g., analgesics, such as opiates) for transdermal delivery to the subject with the selected cannabinoid. Suitable adhesives for use in such matrix-type transdermal patches include polyisobutylenes, acrylates, silicone, and combinations thereof.

Still other patches suitable for use in the practice of the present invention include those described in U.S. Pat. No. 5,223,262 to Kim et al., which is hereby incorporated by reference.

In another illustrative embodiment, the bandage, pad, or other type of patch can be one which is capable of controlling the release of the cannabinoid such that transdermal delivery of the cannabinoid to the subject is substantially uniform and sustained over a period of at least 12 hours, such as at least 24 hours, at least 48 hours, and/or at least 4 days. Such a bandage, pad, or other type of patch which can be used in the practice of the method of the present invention can take the form of an occlusive body, such as the occlusive body described below. In practice, the occlusive body which includes the cannabinoid is positioned on the subject's skin under conditions effective to transdermally deliver the selected cannabinoid to the subject's skin. Such conditions can include, for example, positioning the occlusive body on a portion of the subject's skin which is not covered with hair; where necessary, shaving the hair from the selected portion of the subject's skin; and/or orienting the occlusive body on the skin such that the cannabinoid, when released from the occlusive body, contacts the subject's skin.

In another aspect thereof, the present invention, relates to an occlusive body which includes a cannabinoid; an impermeable backing; and a rate-controlling microporous membrane. The backing and the membrane define a cavity therebetween, and the cannabinoid is disposed within this cavity.

An occlusive body in accordance with the present invention and that is suitable for use in the practice of the method of the present invention is illustrated in FIG. 1.

Referring now to FIG. 1, there is illustrated occlusive body 10. Occlusive body 10 includes impermeable backing 16 having optional polyester face 18, cannabinoid composition 22, and rate-controlling microporous membrane 24. Rate-controlling microporous membrane 24 is shown heat-sealed around the periphery of its upper face to optional polyester face 18 of impermeable backing 16. However, other methods of sealing rate-controlling microporous membrane 24 to impermeable backing 16 (or to optional polyester face 18 of impermeable backing 16) can be employed. Impermeable backing 16 is illustrated as including optional aluminized layer 20 on the outer face thereof. Impermeable backing 16 and rate-controlling microporous membrane 24 define cavity 26, and cannabinoid composition 22 is disposed in cavity 26. Over time, the cannabinoid contained in cannabinoid composition 22 permeates through rate-controlling microporous membrane 24 and optional adhesive layer 14, which is illustrated as being coated on the lower face of rate-controlling microporous membrane 24.

As indicated above, cannabinoid composition 22 contains at least one cannabinoid. Cannabinoids for use in the occlusive body of the present invention can be selected from the group consisting of $\Delta^9$-THC, $\Delta^8$-THC, cannabinol, cannabidiol, nabilone, levonantradol, (−)-HU-210, (+)-HU-210, 11-hydroxy-$\Delta^9$-THC, $\Delta^8$-THC-11-oic acid, CP 55,940, and R(+)-WIN 55,212-2. Preferably, cannabinoids for use in the occlusive body of the present invention are selected from the group consisting of cannabinol, cannabidiol, nabilone, levonantradol, (−)-HU-210, (+)-HU-210, 11-hydroxy-$\Delta^9$-THC, $\Delta^8$-THC-11-oic acid, CP 55,940, and R(+)-WIN 55,212-2. Mixtures of these and other cannabinoids can also be employed. Preferably, the cannabinoid is selected such that it is sufficiently hydrophobic to pass through rate-controlling microporous membrane 24. In addition, cannabinoid composition 22 can also include other inert or active materials, such as those discussed above with regard to topical formulations and/or such as those described below.

Cannabinoid composition 22 can include an aqueous medium, which can contain a water- and oil-miscible solvent. The cannabinoid composition can also contain a material which enhances the cannabinoid's permeation of the skin. Depending on the nature of the chosen solvent, the solvent can also act as the permeation enhancer, or a separate permeation enhancer having the desired miscibility can be added to the cannabinoid composition. Illustrative permeation enhancers that can be used in the occlusive bodies of the present invention include ethanol and oleic acid. Preferably the cannabinoid is present together with at least one diluent so that the cannabinoid accounts for no more than about 25% by weight of the contents of the occlusive body's cavity.

The cannabinoid composition can also include one or more inhibitors of cannabinoid metabolism, particularly in cases where inhibition of cutaneous metabolism is needed to increase therapeutic drug levels. Such inhibitors of cannabinoid metabolism can include inhibitors of the P450 enzymes or other identified critical enzymatic processes. Suitable inhibitors of cannabinoid metabolism include, for example, essential oils which inhibit the activity of cytochrome P450 3A in the skin, such as those described in U.S. Pat. No. 5,716,928 to Benet et al., which is hereby incorporated by reference. Some of these essential oils may also act as transdermal penetration enhancers, thus providing a dual mechanism of percutaneous penetration increase.

Rate-controlling microporous membrane 24 can optionally be made of a single-ply material, or it can be made of a multi-ply material. Only the inner layer of such a membrane needs to be hydrophobic (in the case that the cavity contents are hydrophilic) or hydrophilic (in the case that the cavity contents are hydrophobic). Thus, in one embodiment, an additional permeable membrane is in contact with exterior surface 28 of rate-controlling microporous membrane 24, and the additional permeable membrane has wetting properties which are the same as, or different from the wetting properties of rate-controlling microporous membrane 24.

It is believed that the greater the difference in wetting properties between the cavity contents and rate-controlling microporous membrane 24 (or the innermost layer of rate-controlling microporous membrane 24 if a multi-ply membrane is used), the wider the range of useful solvents and the more linear the release of the drug. Accordingly, it is desirable to employ either a strongly hydrophobic or a strongly hydrophilic rate-controlling microporous membrane 24 (or the innermost layer of the rate-controlling microporous membrane 24 if a multi-ply membrane is used) in conjunction with strongly hydrophilic cavity contents and strongly hydrophobic cavity contents, respectively. It should be noted that the cavity contents can be made hydrophilic by adding surface-active agent, such as an anionic surface-active agent (e.g., sodium lauryl sulphonate), a cationic surface active agent (e.g., cetrimide), or a non-ionic surface active agent (e.g., TWEEN 20®).

Occlusive body 10 can also have an outer layer of an impervious material, such as a layer of aluminum foil or other metal or plastic laminate, to prevent seepage or leaching of the contents of the cavity 26. The cavity side of rate-controlling microporous membrane 24 can be faced with an area-reducing mesh formed, for example, from a non-woven fabric or from a perforated impermeable material such as aluminum foil.

Rate-controlling microporous membrane 24 can be made of any suitable membrane material, such as a hydrophobic and microporous membrane material, for example, CELGARD® 2500 polypropylene of thickness 0.025 mm (1 mil) and pore size 0.4-0.04 microns.

Exterior surface 28 of rate-controlling microporous membrane 24 (i.e., the face distant from cavity 26) can optionally be coated with adhesive layer 14, for example, having a thickness of, for example, about 30 micrometers. Any suitable dermatologically acceptable pressure sensitive adhesive that does not react chemically with the cavity contents or prevent passage of the cannabinoid through the membrane from being rate-controlling can be used for adhesive layer 14. Thus, the adhesive can be chosen such that the cannabinoid passes reasonably rapidly through adhesive layer 14, though some retardation is acceptable in practice. The adhesive can be, for example, an elastomeric silicone polymer. Other suitable adhesives include polyisobutylenes and acrylates. Optional release liner 12, such as a sheet of release coated paper or other material, can be used to cover adhesive layer 14 until the occlusive body 10 is to be used, thus preventing cannabinoid permeation prior to contacting occlusive body 10 with the subject's skin. Immediately prior to use, release liner 12 is stripped from adhesive layer 14, and occlusive body 10 is adhered to the subject's skin (e.g., of the arm) (not shown) by the exposed adhesive layer 14.

It is to be understood that adhesive layer 14 is but one of many suitable ways for attaching the occlusive body 10 to the subject's skin. For example, as an alternative to using adhesive layer 14, a separate tape or bandage material can be employed to attach the occlusive body of the present invention to the subject's skin.

The occlusive body of the present invention can further include a viscous flowable gel which is disposed within the occlusive body's cavity and which immobilizes the cannabinoid within the cavity. Such gel formulations can be useful to reduce the likelihood of abrupt absorption of the cannabinoid in the event of sudden rupture of the cavity and release of the cavity contents onto the skin. Suitable gel formulations can be achieved by making the viscosity of the cavity contents sufficiently high such that they are resistant to spreading in the event of cavity puncture. Illustratively, methyl cellulose in water can be used as a viscosity modifier in such gel formulations. In certain situations, the use of methyl cellulose in combination with the cannabinoid composition can also be advantageous in that the methyl cellulose can also function as a surface active agent to enhance the hydrophilicity of the cavity contents.

The cannabinoid may be mixed with up to 2% (typically about 1% by weight) of oil of *Melaleuca alternifolia* (Tea Tree Oil) or another bactericide before being introduced into the cavity. Tea Tree Oil or another bactericide can also be mixed with an adhesive to form a layer covering a face of the rate-controlling microporous membrane remote from the cavity. The major constituents of Tea Tree Oil are 1-terpinen-4-ol and terpinene with minor amounts of 1,8-cineole and p-cymene, and its properties, together with those of other Australian essential oils, are described in Beylier, *Perfumer & Flavorist*, 4:23 (April/May 1979), which is hereby incorporated by reference. Tea Tree Oil may be substituted by other essential oils that possess antibacterial qualities. Preferably the Tea Tree Oil is present in an amount of from 0.05% to 2% by weight of the liquid contents of the cavity.

In this invention, the rate-controlling microporous membrane can be a hydrophobic microporous material, such as hydrophobic microporous polypropylene or polyethylene. The cavity contents can illustratively include, in addition to the cannabinoid, a wetting agent water based gel formed, for example, using methyl cellulose. As a further illustration of an occlusive body of the present invention, the rate-controlling microporous membrane can be a hydrophobic microporous polypropylene membrane and the cavity can contain, in addition to the cannabinoid, a water-based gel containing an amount of methyl cellulose (e.g., 5%) which gives a linear release of the cannabinoid while retaining water and solids. It may be expedient to dissolve the cannabinoid in an appropriate pharmaceutically acceptable vehicle, which will carry the active substance through the rate-controlling microporous membrane. Moreover, the rate of delivery of the cannabinoid through the rate-controlling microporous membrane into the blood stream of the subject can be varied by varying the surface area, thickness, and composition of the membrane; by varying the weight ratio of cannabinoid-to-vehicle; and by varying the hydrophilicity of the cavity contents.

In this manner, the dosage rate can be varied over a wide range by suitable adjustment of various parameters of the occlusive body, while maintaining a substantially uniform dosage rate. However, in order to minimize variations in dosage rate between different patients owing to variations in their skin resistance, the permeability of the rate-controlling microporous membrane is preferably less than (e.g., from 0.75 to 0.9 times) the permeability of the least permeable skin likely to be encountered in the use of the occlusive body.

Further details with regard to the construction and configuration of occlusive bodies suitable for use in the practice of the present invention can be found, for example, in U.S. Pat. No. 5,254,346 to Tucker et al., which is hereby incorporated by reference. It should be understood that, in addition to the aforementioned cannabinoid or combination of cannabinoids, other active materials, such as opiates and other analgesics, can be contained in the occlusive body's cavity and delivered transdermally through the rate-controlling microporous membrane together with the cannabinoid or cannabinoid combination.

The present invention, in yet another aspect thereof, relates to a method for assessing the permeability of skin to cannabinoids, particularly lipophilic cannabinoids.

The method includes providing a skin sample. Suitable skin samples can be obtained, for example from abdominal plastic surgery procedures. Typically, the sample is dermatomed to a thickness of from 150-600 µm, preferably from 200-300 µm, more preferably around 250 µm. The dermatomed skin sample is generally substantially planar and has a first surface and an opposing second surface.

The method further includes providing a donor solution which includes the cannabinoid to be studied dissolved in a suitable vehicle. Preferably, the vehicle is chosen such that a substantial concentration is achieved and such that, at this substantial concentration, the cannabinoid forms a near (e.g., greater than 80%) saturated solution.

The method further includes providing a receiver solution which includes from 0.1 to 5% of a polyoxyethylene oleyl ether. Suitable polyoxyethylene oleyl ethers include polyoxyethylene 20 oleyl ether, e.g., BRIJ® 98, which is available from Sigma (St. Louis, Mo.). Illustratively, the concentration of polyoxyethylene 20 oleyl ether can be from about 0.1 to about 5%, such as from about 0.2 to about 4%, from about 0.2 to about 3%, from about 0.3 to about 3%, from about 0.4 to about 3%, from about 0.5 to about 3%, from about 0.5 to about 5%, and/or about 0.5%.

In the practice of the method of the present invention, the skin sample is disposed between the donor solution and the receiver solution such that the skin sample separates the donor solution and the receiver solution, such that the donor solution is in contact with the skin sample's first surface, and such that the receiver solution is in contact with the skin sample's second surface. Preferably, the skin sample is arranged such that the epidermal side of the skin sample is in contact with the donor solution. The arrangement of donor solution/skin sample/receiver solution can be held in place using any suitable apparatus. One suitable commercially available apparatus is the PermeGear In-Line Diffusion Cell, which is available from PermeGear, Inc. (Riegelsville, Pa.). Typically the donor solution is permitted to remain in contact with the skin sample for a period of time ranging from several minutes to several weeks (e.g., 2-4 days), during which time some portion of the cannabinoid permeates through the skin sample and into the receptor solution. The method further includes detecting cannabinoid present in the receiver solution, such as by chromatography (e.g., HPLC). The method can further include quantifying the amount of cannabinoid present in the receiver solution, calculating permeability rates, lag times, and other such useful information, as described further below.

The present invention is further illustrated with the following examples.

EXAMPLE 1

Delivery of WIN 55,212-2 Across Skin

WIN 55,212-2 Mesylate (melting point 244-245° C.) was purchased from Research Biochemicals International, Natick, Mass. Reagent-grade chemicals were used as received.

The skin permeation study was carried out using skin excised during abdominal reduction surgery. The skin sample was harvested from the abdomen using a Padgett dermatome set to 250 µm; the skin sample was frozen at −20° C. for one week. The frozen skin sample was thawed and used at the 250 µm split-thickness for the diffusion study. Three PermeGear In-Line Flow Cells were used for the skin permeation study. The receiver fluid was 6% BRIJ® 98 (Polyoxyethylene 20 Oleyl Ether), in order to increase the partitioning of this extremely lipophilic drug into the receiver. The receiver fluid was pumped through the diffusion cells at a rate of one milliliter per hour. The receiver samples were refrigerated until HPLC analysis. The temperature of the diffusion cells was maintained at 32° C. with a circulating water bath. The diffusion experiment was initiated by charging the donor compartment with 0.25 mL of WIN 55,212-2 Mesylate in propylene glycol (50 mg/mL). Water was not used as the drug vehicle, in order to prevent the low water solubility of WIN 55,212-2 from significantly influencing the diffusion rate.

Samples were analyzed using a HPLC system which consisted of a Waters 717 Autosampler, 501 Pumps, and a 484 Tunable UV Absorbance Detector with Millennium Chromatography Software. A reversed phase Beckman 5 µm particle 4.6 mm×25 cm C-18 column was used with the UV detector set at a wavelength of 215 nm. The mobile phase consisted of 0.05 M monobasic potassium phosphate:acetonitrile (300 mL:700 mL) at a flow rate of 2 mL/min. The sensitivity of the assay was 10 ng/mL, and the WIN 55,212-2 had a retention time of 3.4 minutes. Standard curves exhibited excellent linearity over the entire concentration range employed in the assays.

Figure 2:
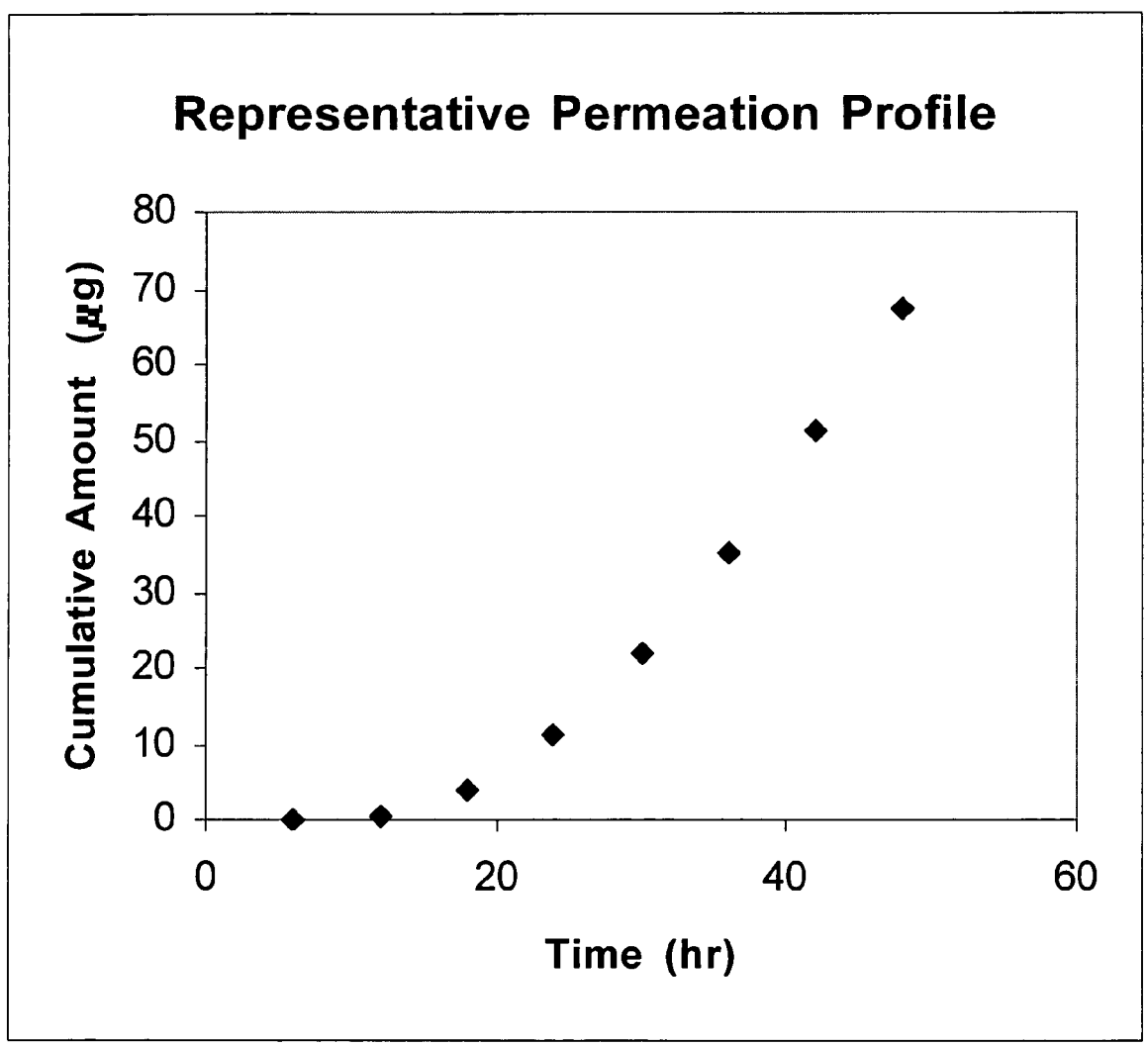
FIG. 2 is a permeation profile of showing the delivery of a cannabinoid across skin.

Skin permeation data were plotted as the cumulative amount of drug collected in the receiver compartment as a function of time. The lag times and steady-state fluxes were calculated using the terminal, linear portions of these curves. The slopes ($J_s$) through these curves were determined using linear regression analysis. In all cases, the coefficients of determination for the lines were >0.99. A representative permeation profile is shown in FIG. 2.

Lag times were determined by extrapolating the steady-state curves to the X-axis. The permeability coefficient was calculated from Fick's law of diffusion:

$$\frac{1}{A}\left(\frac{dM}{dt}\right) = J_s = K_P \Delta C \qquad \text{Eq. 1}$$

where $J_s$ is the steady-state flux (e.g., in [g/cm²/h]), M is the cumulative amount of drug permeating the skin, A is the area of the skin, $K_p$ is the effective permeability coefficient in cm/h, and $\Delta C$ is the difference in concentrations of cannabinoid in the donor and receiver compartments.

The skin permeation experiment was run for 48 hours, during which time a steady-state flux was obtained. The diffusion lag time for these experiments averaged to be 24 hours. Although the donor compartment did not contain a saturated drug solution, the drug depletion from the donor compartment was minimal (<1%). The mean flux of these diffusion experiments was found to be 2.6 (±1.1 standard deviation, n=3) µg/cm²/h. The effective permeability coefficient, P, was calculated using Fick's law of diffusion as 1.4×10-8 cm/s.

These diffusion values are similar in magnitude to the reported full-thickness human skin $\Delta^8$-THC flux rate of 3.5 µg/cm²/hr, and the permeability coefficient of 3.6×10$^{-8}$ cm/s reported in Touitou et al., Int. J. Pharm., 43:9-15 (1988), which is hereby incorporated by reference. The WIN 55,212-2 flux would have been a higher value if enough drug had been available to apply a saturated solution to the skin. One of the practical goals elucidated from this skin permeation study is to choose a vehicle that solubilizes enough drug, but not so much drug that making a saturated solution becomes excessively expensive.

EXAMPLE 2

Optimization of in vitro Experimental Conditions for Studying Permeation Through and Metabolism of Cannabinoids by Human Skin The permeability of human skin has been studied for several decades. The skin consists of two major layers, the outer epidermis and the inner dermis. The stratum corneum ("SC"), the outermost 10-20 μm of the epidermis, is responsible for the skin's excellent diffusional resistance to the transdermal delivery of most drugs. Most of the skin's enzymatic activity lies in the basal cell layer of the viable epidermis. Fibrous collagen is the main structural component of the dermis. The skin vasculature is supported by this collagen and lies a few microns underneath the epidermis. Basically, it is here that permeation ends and systemic uptake begins. Many researchers have developed skin permeability relationships based on the physicochemical parameters (molecular weight, molecular volume, lipophilicity, hydrogen-bonding potentials, polarity, etc.) of skin penetrants. However, when dealing with transdermal administration of cannabinoids, these skin permeability relationships need to be modified to take into account the potential complications of extreme lipophilicity and concurrent metabolism of these drugs.

Generally speaking, cutaneous metabolism of transdermally delivered drugs is a potential pitfall to therapeutic success. For example, transdermally delivered testosterone and estradiol undergo significant cutaneous metabolism. However, as discussed further below, cutaneous metabolism of cannabinoids can be exploited when designing transdermal prodrugs or when delivering drugs that are converted to active metabolites. For example, it is likely that cannabinoids undergo significant metabolism as they diffuse through viable human skin. The low oral bioavailability of dronabinol (0.1-0.2) is an indication that extensive metabolism may occur; however, some compounds that undergo extensive systemic metabolism do not undergo biotransformation during transit through the skin (Collier et al., "Cutaneous Metabolism," pp. 67-83 in Bronaugh et al., eds., IN VITRO PERCUTANEOUS ABSORPTION: PRINCIPLES, FUNDAMENTALS, AND APPLICATIONS, Boca Raton, Fla.: CRC Press (1991), which is hereby incorporated by reference). Most enzymes in the skin have 1-10 percent of the enzymatic specific activity they have in the liver, although other enzymes have equivalent specific activity in both organs. Oxidation generates the main metabolites of $\Delta^8$-THC and $\Delta^9$-THC, by aliphatic hydroxylation at the eleven-position carbon, further oxidation to an 11-oic acid, and subsequent glucuronidation. Nabilone forms a diol by reduction at the 9-keto group. Levonantradol is rapidly deacetylated. Evidence suggests that CP 55,940 may undergo side chain hydroxylation.

Selection and optimization of cannabinoids for transdermal delivery requires an understanding of their cutaneous metabolism. Furthermore, since skin metabolism of topical in vivo studies cannot easily be distinguished from blood, liver, or other tissue metabolism, cutaneous metabolism is better studied in vitro. However, the success of any such in vitro study depends heavily on finding ideal conditions to simulate in vivo conditions, especially in maintaining tissue viability. Thus, selection of an optimal receiver solution is critical to the success of any such in vitro studies.

Therefore, applicant has undertaken a study to optimize in vitro experimental conditions for the measurement of $\Delta^9$-tetrahydrocannabinol across human skin. Additionally, intact and stripped skin were also compared in order to determine if the SC provided significant resistance to the diffusion of highly lipophilic $\Delta^9$-tetrahydrocannabinol. The study and results are described below.

$\Delta^9$-tetrahydrocannabinol in 95% ethyl alcohol was obtained in ampules from National Institute of Drug Abuse (Research Triangle Park, N.C.). Hanks balanced salts modified powder, Bovine Albumin Fraction V ("BSA"), potassium phosphate monobasic anhydrous, sodium bicarbonate, and Polyoxyethylene 20 Oleyl Ether (BRIJ 98®) were obtained from Sigma (St. Louis, Mo.). Propylene glycol, 4-(2-hydroxyethyl)-1-piperazineethanesulfonic acid ("HEPES"), triethylamine ("TEA"), gentamycine sulfate, acetonitrile (HPLC grade) and 20 mL Scintillation vials were obtained from Fisher Scientific (Fairlawn, N.J.).

The following instruments and accessories were used in this study. PermeGear flow-through diffusion cells having a surface area of 0.95 $cm^2$ were obtained from PermeGear (Hellertown, N.J.). Water Bath 280 series and Shallow Form Shaker Bath were obtained from Precision (Winchester, Va.). Isotemp 2006S water circulator was obtained from Fisher Scientific (Fairlawn, N.J.). Retriever IV fraction collector was obtained from ISCO Inc. (Lincoln, Nebr.). PUMPPRO® MPL static pump was obtained from Watson Marlow (Wilmington, Mass.). Sartoris BP211D model balance was obtained from Sartoris (Edgewood, N.Y.). Padgett Dermatome was obtained from Padgett Instruments (Kansas City, Mo.). HPLC with autosampler (200 series model) and UV detector 785A were obtained from Perkin Elmer. Autosampler vials, nonsilanized/silanized were obtained from Kimble Glass (Vineland, N.J.). All glassware employed in the study was sterilized with 70% v/v ethanol/water.

Receiver solutions containing Hanks-HEPES balanced salt solution ("HHBSS") and BSA were prepared as follows. HHBSS was prepared by dissolving 9.8 g Hanks balanced salt mixture along with 5.96 g of HEPES and 0.35 g of sodium bicarbonate in 1000 mL of Mili-Q distilled water. The pH was adjusted to 7.4 with 1 N HCl or 1 N NaOH, the solution was filtered through a Milipore filtration system using a 0.2 μm membrane, and 50 mg of gentamycin was added to minimize microbial contamination. Appropriate amounts of BSA, either 4% or 6% (based on the experimental design), were then dissolved into the resulting solutions to produce the HHBSS/BSA receiver solutions.

Receiver solutions containing BRIJ® 98 were prepared by dissolving appropriate amounts of BRIJ® 98 (0.5% and 6% w/v) in 1000 mL of Mili-Q distilled water.

Human skin samples were prepared as follows. Skin tissue samples from patients having undergone abdominoplasty were obtained from National Cancer Institute Cooperative Human Skin Tissue Network. The samples were dermatomed immediately upon arrival (usually less than 24 hr after harvesting) to obtain 250 μm intact skin samples. The samples were either used immediately or wrapped and then frozen at −20° C. The required fresh tissue portions for immediate use were sliced according to diffusion cell disk area. The removed portions were transferred immediately onto diffusion cell disks that had been previously sterilized with 70% v/v ethanol/water, making sure that the dermal portions were exposed towards the receiver solution. The disks were fixed onto their holders with the aid to hold the tissue firmly and to avoid any leakage of formulation. The actual thickness of skin used in each experiment was measured.

Stripped skin samples were obtained from the above-described abdominoplasty skin as follows. The required skin portion was marked before being dermatomed. The SC of the selected portion was removed with help of SCOTCH® book tape No. 845. The procedure was repeated (typically 10-30 times) to make sure that the SC was removed convincingly. The resulting stripped skin, thus obtained, was either used immediately or wrapped and frozen at −20° C. The stripped skin samples were then sliced and transferred onto diffusion cell disks as described above. The actual thickness of skin used in each experiment was measured.

When additional intact and stripped skin samples were needed, frozen intact and stripped skin samples were thawed at room temperature, and the required tissue portions were then sliced and transferred onto diffusion cell disks as described above.

A $\Delta^9$-tetrahydrocannabinol formulation was prepared as follows. Suitable aliquots of $\Delta^9$-tetrahydrocannabinol in 95% absolute ethanol (approximately 0.04 parts ethanol/mL) were transferred to a mixture of propylene glycol:water (90:10) and mixed well to obtain 8.59 mg/mL of drug concentration in each sample.

The in vitro experiments were carried out under the following conditions. The receiver solutions were maintained at 37° C. for 30 min prior to conditioning the diffusion cell lines. After cleaning the transfer tubes with 50% methanol for 1 h, the diffusion lines were conditioned by pumping the receiver solution through them for at least for 1 h. The diffusion cell mounting table (an aluminum block holder) was conditioned to keep the skin surface at 32° C. by circulating a water bath maintained at 37° C. Thereafter, the skin diffusion cell disks were transferred to the mounting table, and the skin diffusion cell disks were equilibrated by circulating a water bath maintained at 37° C. for 30 min. The donor cell was loaded with 240 µL of the $\Delta^9$-tetrahydrocannabinol formulation and was covered with a suitable cap. The receiver solution was pumped through the receiver cell at a flow rate of 1.5 mL/h for either 48 h or 96 h. Samples were collected using a fraction collector at 6 h intervals for either 48 h or 98 h, depending on the study. At the end of each experiment, the tissue was removed from the respective diffusion cell disk. Both the epidermal and dermal surfaces of the removed tissue sample was briefly washed with distilled water, and excess water was removed with blotting paper. The formulation covered skin surface of the washed and blotted removed tissue sample was stripped once with SCOTCH® book tape No. 845 to remove the formulation, and the stripped, washed, and blotted removed tissue sample was sliced to smaller portions. The smaller portions were then transferred to a previously weighed scintillation vial, the combined weight of the scintillation vials and tissue was measured, and, from this, the weight of the tissue was calculated. The tissue samples were then digested overnight in 10 mL ACN on a shaker bath to estimate the drug penetration into skin layers.

BRIJ® 98 pretreatment studies were carried out as follows. At the end of regular 48 h diffusion experiment, the samples collected in BRLI® 98 receiver solution were immediately removed and, without interruption of the experiment, replaced with BSA 4% receiver solution. The experiment was continued for a further 48 h period against both BRIJ® 98 and BSA 4% controls.

The diffusion samples collected using either 4% or 6% BSA receiver solution were extracted in the following manner. To each sample was added 4-fold ACN, and the resulting mixture was vortexed for 1 min, then sonicated for 15 min, then vortexed again for 1 min, and finally centrifuged at 9000 rpm for 15 min. The supernatant was collected and transferred to silanized HPLC autosampler vials. 100 µL of each sample was injected for each HPLC run, and the recovery was 90%.

The diffusion samples collected using either 0.5% or 6% BRIJ® 98 receiver solution were either injected directly into the HPLC apparatus or diluted 1:3 with ACN, vortexed for 1 min, and then injected into the HPLC apparatus. The injection volume was 100 µL, and recovery was 100%.

The diffusion samples were estimated using the following HPLC method. A mobile phase containing 80:20 ACN:phosphate buffer (25 mM $KH_2PO_4$+0.1% TEA, pH 3.0), a reverse phase C8 column (BROWNLEE®, 220×4.6 mm, Spheri-5), and a guard column (BROWNLEE®, reverse phase, C8, 15×3.2 mm, 7 µm particle size) were employed. The flow rate was 1.5 mL/min. Run time was 7.0 min, except that all BRIJ® 98 samples were run for additional 7.0 min after each run time at a flow rate of 2.0 mL/min to wash the column of BRIJ® 98 peaks). The detection wavelength was set to 215 nm, retention time was 4.0±0.1 min, linearity was 25-1000 ng/mL, and sensitivity was 5 ng/mL.

The data were treated as follows. Permeability coefficients of $\Delta^9$-tetrahydrocannabinol were calculated using the steady state skin flux and the saturation solubility of the compound in the vehicle employed.

Figure 3:
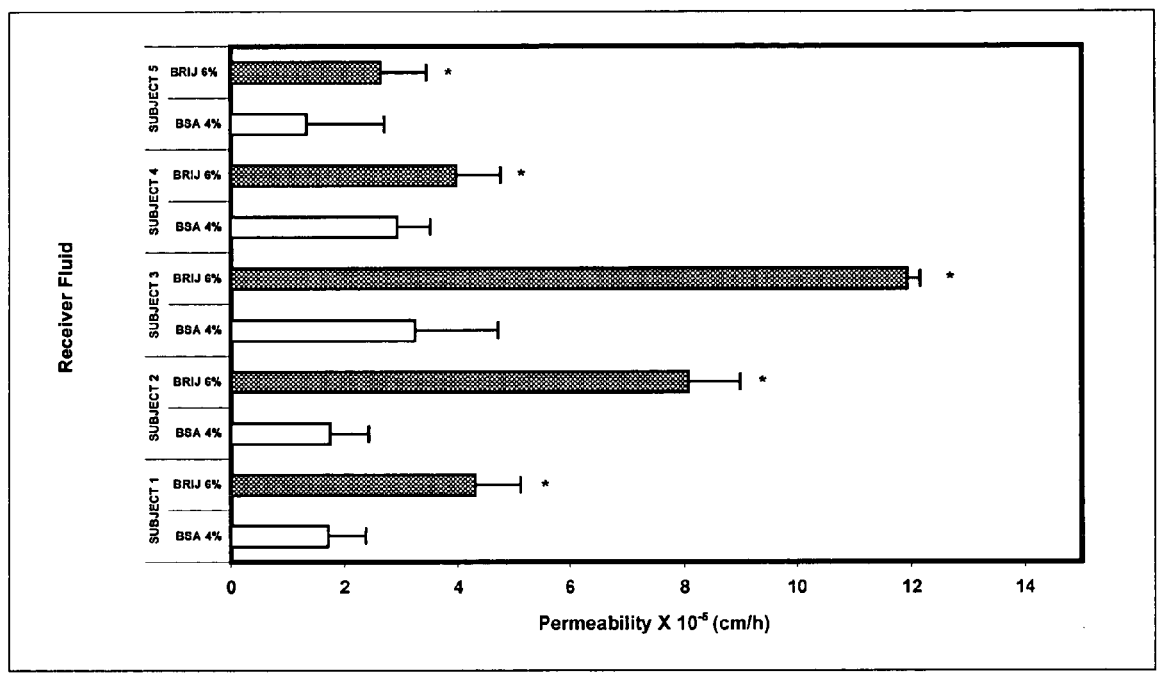
FIG. 3 is a bar graph showing permeability of skin samples to a cannabinoid for various receiver solutions.

FIG. 3 shows the permeability of $\Delta^9$-tetrahydrocannabinol through human skin in five subjects in presence of both BSA (4%) and BRIJ® 98 (6%). It is evident from the data, that permeability of $\Delta^9$-tetrahydrocannabinol is 2-5 fold higher in presence of BRIJ® 98 solution relative to BSA solution, except in subject 4. These differences were statistically significant in all subjects (Student's t-test, $p<0.05$) indicated with asterisk in FIG. 3. No clear pattern between lag times was observed.

Figure 4:
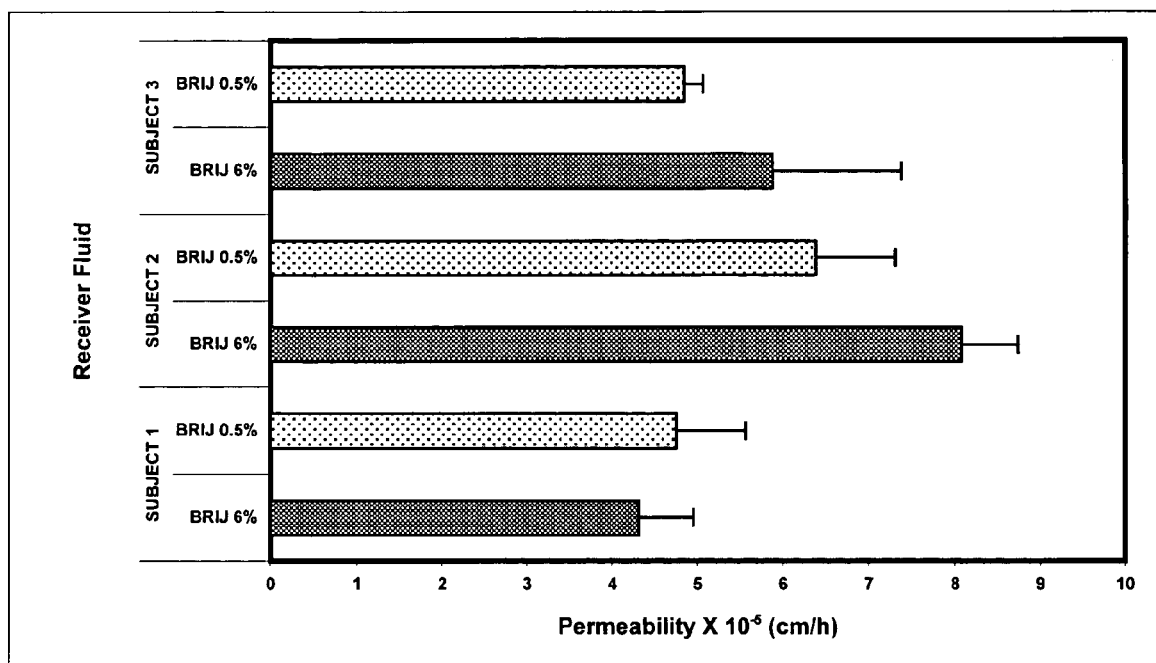
FIG. 4 is a bar graph showing permeability of skin samples to a cannabinoid for various receiver solutions.

The higher permeability of $\Delta^9$-tetrahydrocannabinol noted with BRIJ® 98 (FIG. 3) could be due to possible damage to the skin caused by BRIJ® 98, a surfactant. Therefore, to minimize this possible damage to the skin and to enhance the solubility of drug, results using a low concentration of BRIJ® 98 (0.5% solution) were compared against the results obtained using a 6% BRIJ® 98 solution. The results are set forth in FIG. 4.

Interestingly, similar $\Delta^9$-tetrahydrocannabinol permeability results were obtained for the three subjects irrespective of whether 6% BRIJ® 98 solution or 0.5% BRIJ® 98 solution was employed, and whatever differences exist are not statistically significant (Student's t-test, $p<0.05$). No particular difference was observed between lag times. These findings demonstrate that one can minimize possible damage to skin without adversely affecting the solubility of drug in receiver solution by using a low (e.g., about 0.1 to about 5%, such as about 0.2 to about 4%, about 0.2 to about 3%, about 0.3 to about 3%, about 0.4 to about 3%, about 0.5 to about 3%, and/or about 0.5 to about 5%) concentration of BRIJ® 98.

Figure 5A:
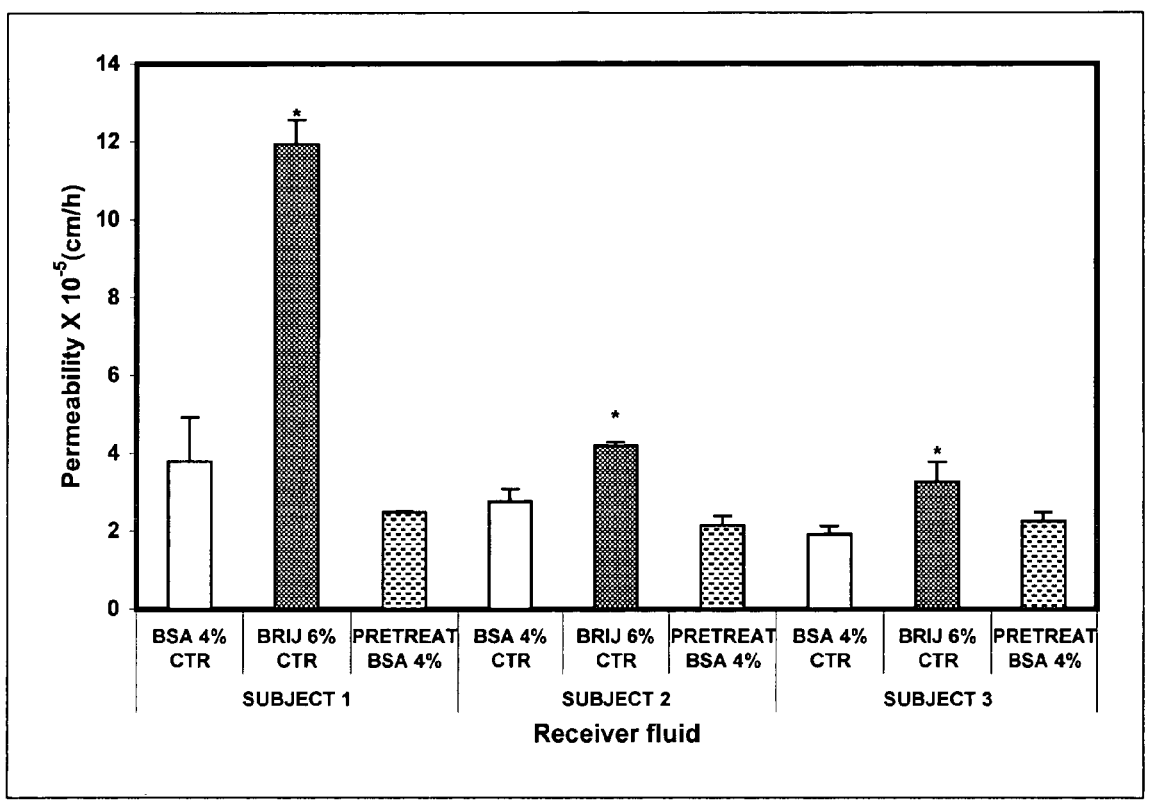
FIG. 5A is a bar graph and FIG. 5B is a permeation profile, each showing permeability of skin samples to a cannabinoid for various receiver solutions.
Figure 5B:
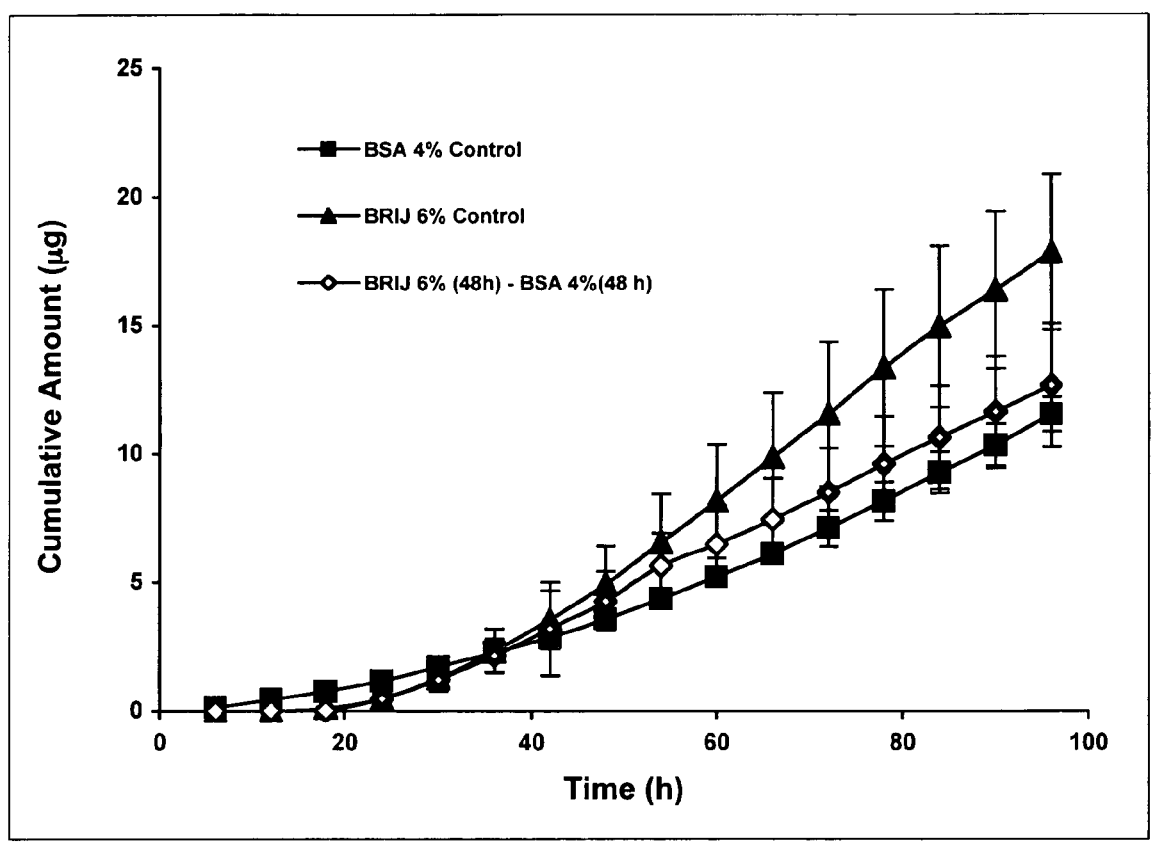

Experiments were conducted in which, at the end of BRIJ® 98 pretreatment period (48 h), the receiver solution was changed to HHBSS/BSA (4%). If BRIJ® was causing damage to the skin sample, this pretreatment step should also result in increased drug permeation in presence of HHBSS/BSA. The results of pretreatment studies performed to understand the possible damage effects of 6% BRIJ® 98 in three subjects are shown in FIG. 5A. The $\Delta^9$-tetrahydrocannabinol permeability obtained between BRIJ® and BSA solutions demonstrated once again that 6% BRIJ® 98 resulted in higher drug permeation through human skin relative to BSA pretreatment and BSA control. Tissues pretreated with 6% BRIJ® 98 for 48 h followed by a change to BSA (4%) for an additional 48 h exhibited permeability values similar to those of 4% BSA control after 96 h. In addition, referring now to FIG. 5B, there is no noticeable deviation from steady state in any of the permeability profile of 6% BRIJ® 98 solutions during 96 h, while, in the pretreated samples, the profile tends to move closer and parallel to the 4% BSA control. No lag time differences between the receiver solutions were observed. From the above discussion and the data presented in FIGS. 5A and 5B, it is clear that BRIJ® does not cause any damage to the skin. The one-way ANOVA and Tukey test comparison of above data suggest that there is significant difference between the permeability values of BRIJ® 98 and 4% BSA solutions (this significance being noted in FIG. 5a with an asterisk) and that there is no significant difference between BSA control and pretreated/BSA solutions.

Figure 6:
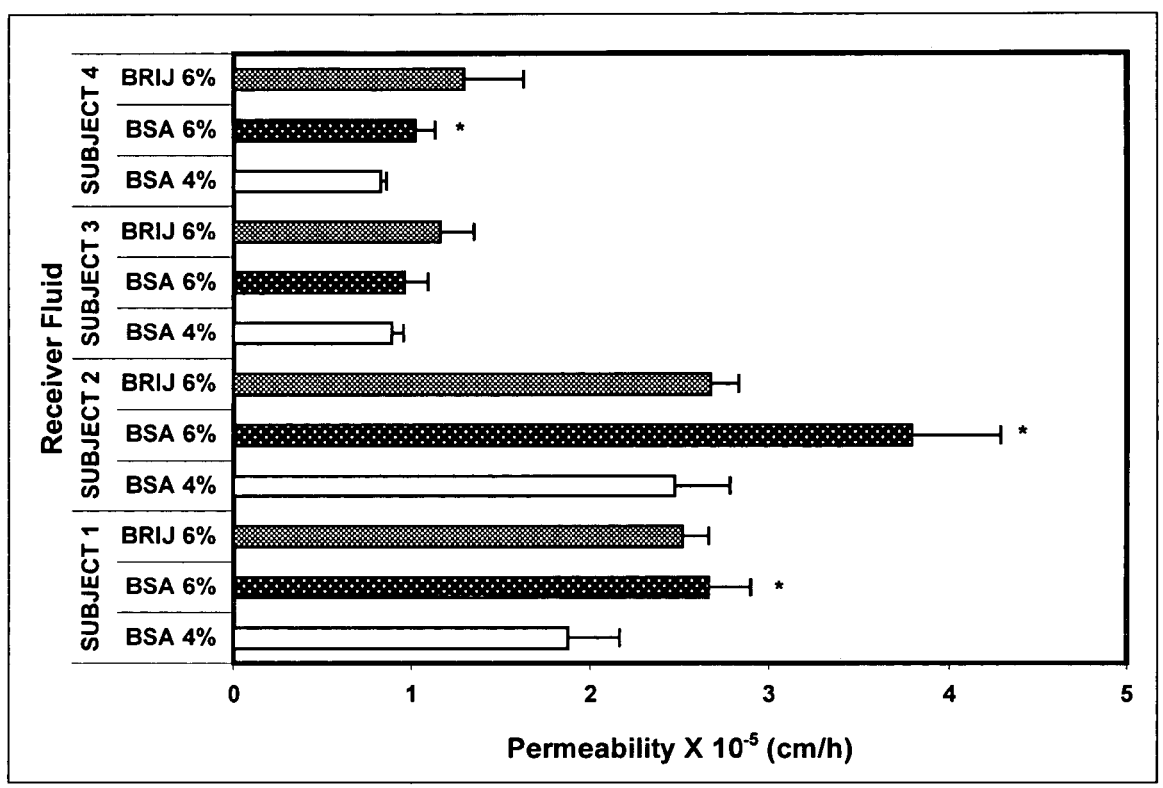
FIG. 6 is a bar graph showing permeability of skin samples to a cannabinoid for various receiver solutions.

As discussed above, it is known that many drugs are metabolized during their permeation across human skin. To understand this metabolic process for cannabinoids and to thus be able to choose those cannabinoids that are likely to be active upon systemic absorption, the receiver solution should be such that it not only has appreciable solubility for the drug but also such that it does not adversely impact on the tissue's viability. In this context, HHBSS/BSA, being closer in composition to systemic fluids especially blood, can be considered a better receiver solution. Accordingly, experiments were conducted using 6% BRIJ® 98, 4% BSA, and 6% BSA. The results obtained from this study in four subjects are shown in FIG. 6. It is clear from the data presented in FIG. 4 that 6% BSA has enhanced $\Delta^9$-tetrahydrocannabinol permeability in all subjects by some 20-50% relative to 4% BSA (except in subject 3). Additionally, in three out of four subjects in FIG. 6, the permeability difference between 6% BSA and 4% BSA was considered to be statistically significant (Student's t-test, p<0.05). No lag time differences between receiver solutions were observed.

Figure 7:
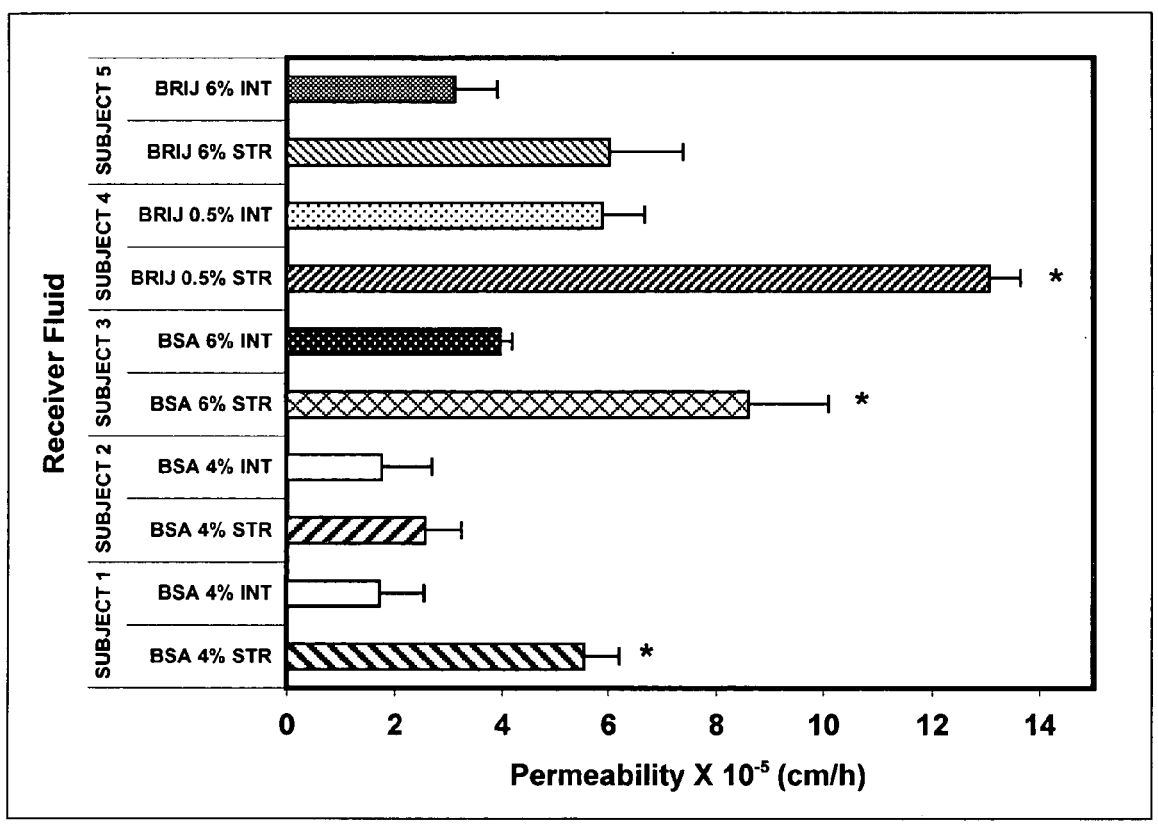
FIG. 7 is a bar graph showing permeability of stripped and intact skin samples to a cannabinoid for various receiver solutions.

It is conventional practice to perform tape strip studies against intact skin to understand clearly the barrier effects of SC. Thus, tape strip studies for $\Delta^9$-tetrahydrocannabinol against intact skin were conducted using the above-identified receiver solutions. The results obtained in various subjects are shown in FIG. 7. It is clear from FIG. 7 that the permeability values of tape stripped skin are 2-3 times higher relative to their intact skin counterparts, and, in the case of 6% BRIJ® 98 receiver solution, a six fold difference was observed. Moreover, the observed mean lag times were found to be shorter for stripped skin (7.8±3.9 h) relative to intact skin (18.0±3.4 h). The Student's t-test (p<0.05) comparison of data suggests that the permeability differences were significant in three out of five subjects. This demonstrates that the SC acts as barrier for permeation of $\Delta^9$-tetrahydrocannabinol molecule.

EXAMPLE 3

Figure 8:
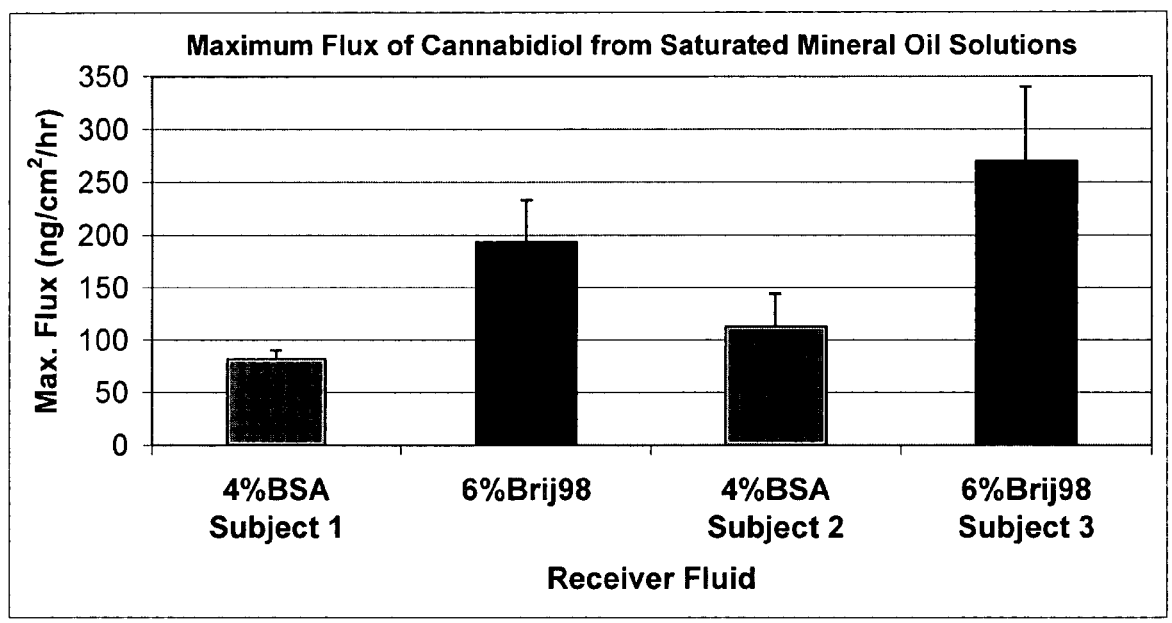
FIG. 8 is a bar graph showing maximum flux of a cannabinoid through skin samples for various receiver solutions.

Delivery of 2-[3-methyl-6-(1-methylethenyl)-2-cyclohexen-1-yl]-5-pentl-1,3-benzenediol Across Skin The flux of 2-[3-methyl-6-(1-methylethenyl)-2-cyclohexen-1-yl]-5-pentyl-1,3-benzenediol (a cannabidiol) ("CBD") across human skin was measured following the procedures set forth in Example 2, except that the donor compartment was charged with CBD in mineral oil (saturated) instead of Example 2's $\Delta^9$-tetrahydrocannabinol in propylene glycol (50 mg/mL). Two receiver solutions were employed: 4% BSA and 6% BRIJ® 98. The experiments were run as in Example 2, and the maximum flux was calculated. The results are presented in FIG. 8.

A number of compounds may be useful in enhancing the transdermal permeation of cannabinoids by increasing the amount of a co-administered cannabinoid within a patient's skin. Suitable permeation ehnancers include, for example, propylene glycol monolaurate, diethylene glycol monoethyl ether, oleoyl macrogolglycerides, caprylocaproyl macrogolglycerides, and oleyl alcohols.

EXAMPLE 4

Co-Administration of Cannabinoids and Permeation Enhancers

The aim of the experiment was to evaluate the effect of permeation enhancers on human skin permeation of cannabidiol (CBD). The following permeation enhancers were used in the study:
LAUROGLYCOL 90-(Propylene glycol monolaurate 90%)-LG-90
TRANSCUTOL HP (Purified diethylene glycol monoethyl ether)-TC-HP
LABRAFIL® M 1944 CS (Oleoyl Macrogolglycerides)-LF
LABRASOL® (Caprylocaproyl Macrogolglycerides)-LB
SUPER REFINED® NOVOL NF (Oleyl Alcohol)-OA A high-pressure liquid chromatography (HPLC) assay was used for the analysis of CBD in the samples. The HPLC system consisted of a Waters 717 plus Autosampler, Waters 1525 Binary HPLC Pump and Waters 2487 Dual $\lambda$ Absorbance Detector with Waters Breeze software. A Brownlee C-18 reversed-phase Spheri-5 µm column (220×4.6 mm) with a C-18 reversed phase 7 µm guard column (15×3.2 mm) was used with the UV detector set at a wavelength of 215 nm. The mobile phase was comprised of acetonitrile: 25 mM phosphate buffer with 0.1% triethylamine pH 3.0 (80:20). The flow rate of the mobile phase was 1.5 mL/min and 100 µL of the sample was injected onto the column. The external standard curve exhibited excellent linearity over the entire concentration range employed in the assays.

Human skin harvested during abdominoplasty was used for the diffusion studies. Skin sections were obtained by using a Padgett Instruments® dermatome set to 250 microns and stored at −20° C. A PermeGear flow-through (In-Line, Riegelsville, Pa.) diffusion cell system was used for the skin permeation studies. Trans-epidermal water loss was measured (Evaporimeter EP1™, ServoMed, Sweden) after securing the skin in the cells. Pieces of skin with readings below 10 g/m²/h were used for the diffusion studies. The skin surface in the diffusion cells was maintained at 32° C. with a circulating water bath. The receiver solution was HEPES-buffered Hanks' balanced salts with gentamicin (to inhibit microbial growth) containing 40% polyethylene glycol 400 (pH 7.4), and the flow rate was adjusted to 1.1 mL/h. An excess quantity of CBD was added to the donor vehicle (propylene glycol: Hanks' buffer (80:20)) solution with and without permeation enhancers at 6% v/v, sonicated for 10 min, and then applied onto the skin. Excess quantity of the drug was used in the donor compartment throughout the diffusion experiment in order to maintain maximum and constant chemical potential of the drug in the donor vehicle. Each cell was charged with 0.25 mL of the respective drug solution. Samples were collected in 6 h increments for 48 h. All the samples were stored at 4° C. until HPLC analysis.

The cumulative amount of drug collected in the receiver compartment was plotted as a function of time. The flux value for a given experiment was obtained from the slope of the steady state portion of the cumulative amount of drug permeated plotted over time. Apparent permeability coefficient values were computed, as described above, from Fick's First Law of Diffusion:

$$\frac{1}{A}\left(\frac{dM}{dt}\right) = J_s = K_p \Delta C$$

Sink conditions were maintained in the receiver throughout the experiment, so $\Delta C$ was approximated by the drug concentration in the donor compartment.

Drug disposition in the skin samples was measured at the completion of the 48 h experiment. The skin tissue was rinsed with nanopure water and blotted with a paper towel. To remove the drug formulation adhering to the surface, the skin was tape stripped twice using book tape (Scotch®, 3M, St. Paul, Minn.). The skin in contact with the drug was excised, minced with a scalpel and placed in a pre-weighed vial. Drug was extracted from the skin by equilibrating with 10 mL of ACN in a shaking water bath overnight at room temperature. Samples were analyzed by HPLC to determine CBD content in micromoles (µmol) of drug per gram of wet tissue weight.

Statistical analysis of the in vitro human skin permeation data was performed using SigmaStat 2.03. A one-way ANOVA with Tukey post-hoc analysis was used to test the statistical differences among the different treatments.

The results of the permeation studies were as follows:

TABLE 1

| Formulation | Flux (nmol/cm$^2$/h) | Lag time (h) | Cumulative amount permeated at 48 h (nmol) | Skin content (µmol/g) |
|---|---|---|---|---|
| CBD‡* | 6.13 ± 0.43 | 14.79 ± 1.59 | 193.21 ± 22.77 | 22.28 ± 24.47 |
| CBD + LG-90† | 11.43 ± 0.76 | 9.20 ± 3.88 | 422.22 ± 63.27 | 19.74 ± 8.40 |
| CBD + TC-HP† | 14.81 ± 1.08 | 12.34 ± 5.78 | 503.98 ± 109.94 | 34.19 ± 20.34 |
| CBD‡ | 9.16 ± 1.41 | 9.43 ± 2.47 | 338.11 ± 73.09 | 9.08 ± 6.12 |
| CBD + LB* | 12.45 ± 0.94 | 4.57 ± 2.72 | 514.32 ± 64.59 | 24.86 ± 5.33 |
| CBD + OA* | 14.69 ± 1.70 | 5.70 ± 0.00 | 688.09 ± 154.29 | 37.94 ± 3.66 |
| CBD + LF* | 14.90 ± 3.02 | 1.92 ± 2.05 | 670.54 ± 184.73 | 59.03 ± 26.36 |

Figure 9:
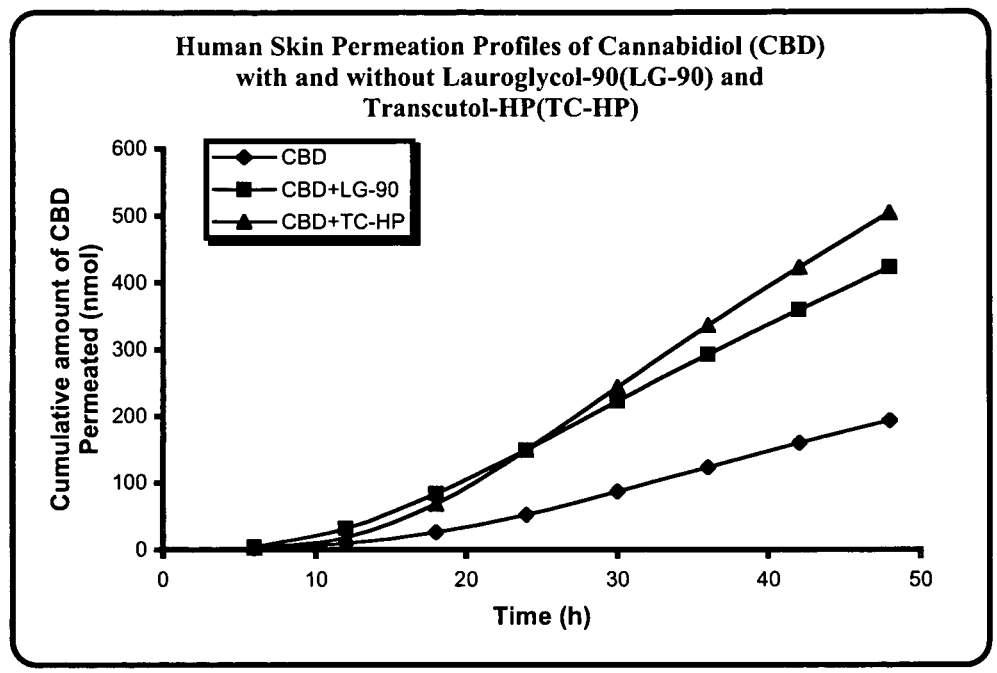
FIG. 9 is a permeation profile showing the delivery of cannabidiol using permeation enhancers.
Figure 10:
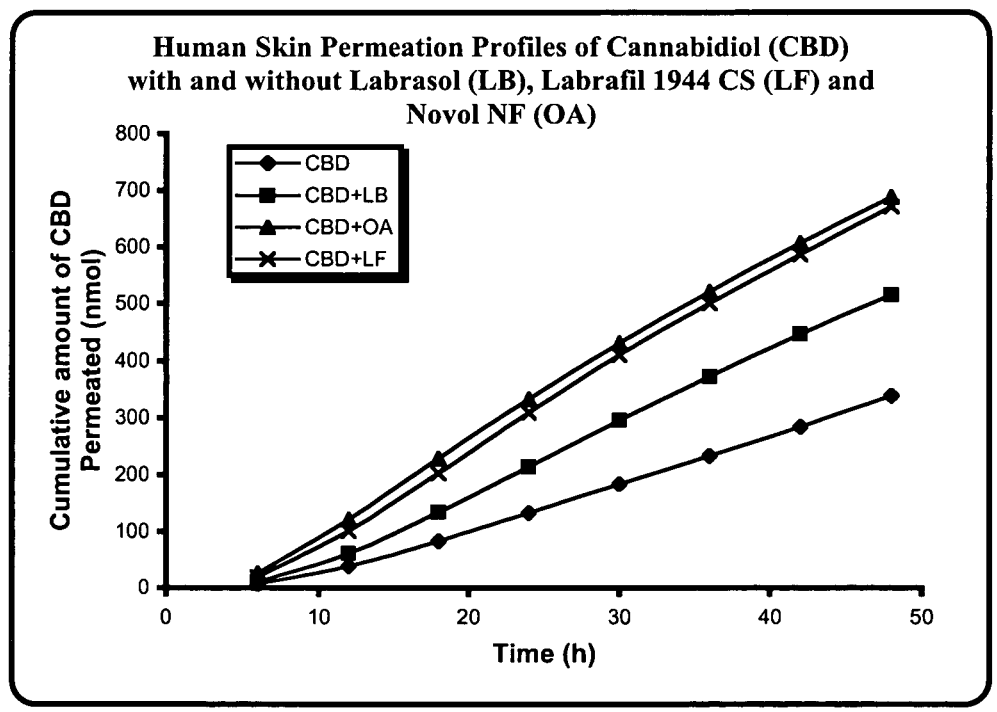
FIG. 10 is a second permeation profile showing the delivery of cannabidiol using permeation enhancers.

*n = 3;
†n = 4;
‡Experiments were run with skin from two different human subjects The results of the present study indicated that CBD can be delivered via the transdermal route and that the permeation enhancers, Lauroglycol-90 (Propylene glycol monolaurate 90%), Transcutol-HP (Purified diethylene glycol monoethyl ether), LABRASOL® (Caprylocaproyl macrogolglycerides), SUPER REFINED® NOVOL NF (Oleyl Alcohol) and LABRAFIL® M 1944 CS (Oleoyl macrogolglycerides) increased the amounts of CBD permeated through human skin. As shown in Table 1 above and in FIGS. 9 and 10, each enhancer at a 6% v/v concentration in the donor vehicle increased the steady sate flux and cumulative amounts permeated at 48 h significantly (p<0.05) when compared to CBD alone.

A 2.41 and 1.86 fold increase in steady sate flux was observed with Transcutol-HP and Lauroglycol-90, respectively, when compared to the steady sate flux of CBD alone. Transcutol-HP significantly increased the amounts of CBD permeated through human skin when compared to Lauroglycol-90 (p<0.05). A 1.29 fold increase in steady sate flux of CBD was observed with Transcutol-HP when compared to Lauroglycol-90. Whereas, a 1.36, 1.62 and 1.60 fold increases in steady state flux were observed with LABRASOL®, LABRAFIL® M 1944 CS and SUPER REFINED® NOVOL NF (Oleyl Alcohol).

Figure 11:
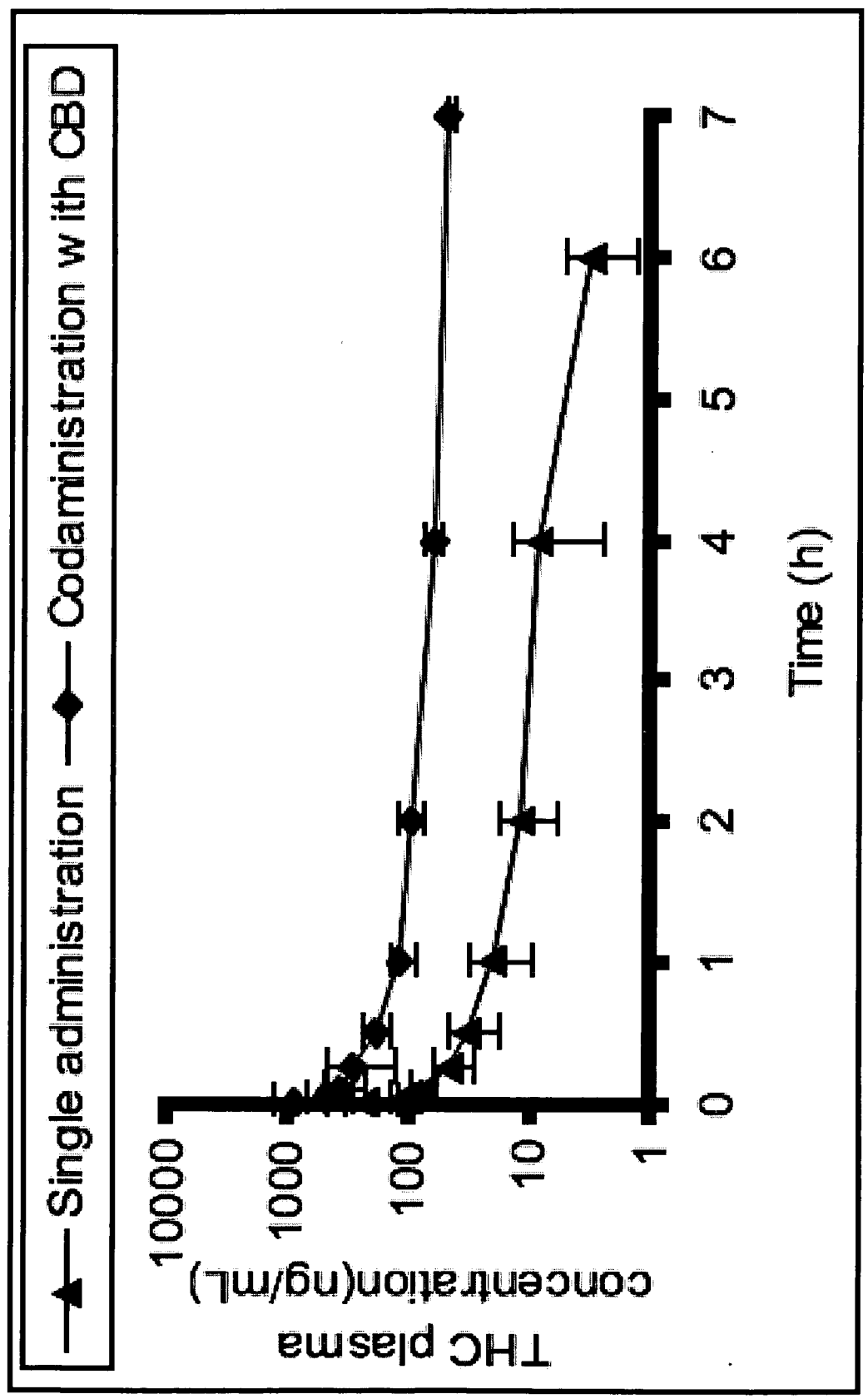
FIG. 11 is a graph of THC plasma concentrations following the administration of THC alone and in combination with cannabidiol.
Figure 12:
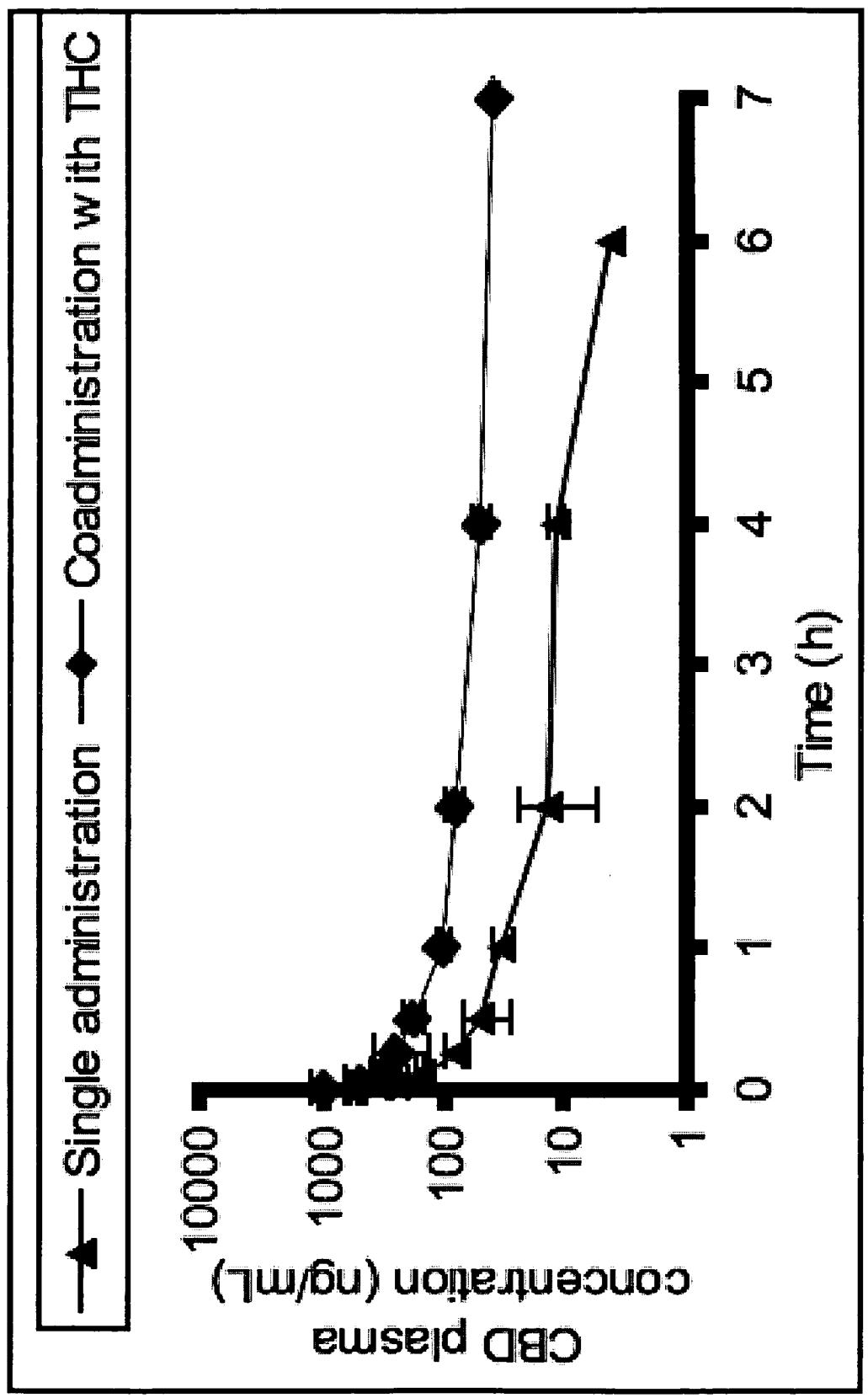
FIG. 12 is a graph of cannabidiol plasma concentrations following the administration of cannabidiol alone and in combination with THC.

FIGS. 11 and 12 show plasma THC and CBD concentrations, respectively, following the separate and coadministration of each. As can be seen, the concentration of each is higher both initially and over time when coadministered.

Overall, the results of the present study indicated that significant amounts of CBD could be delivered through human skin in the presence of permeation enhancers.

The foregoing description of the preferred embodiments of this invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of this invention as defined by the accompanying claims.

The invention claimed is:

1. A method of transdermally administering cannabidiol through the skin of a subject and into the systemic circulation for treating arthritis comprising:
    applying to the skin of the subject a pharmaceutical composition which comprises:
    cannabidiol; and
    (ii) a permeation enhancer consisting of diethylene glycol monoethyl ether.

2. The method of claim 1, wherein diethylene glycol monoethyl ether is present in an amount of about 6% by volume of the pharmaceutical composition.

3. The method of claim 1, wherein the pharmaceutical composition further comprises an analgesic.

4. The method of claim 3, wherein the analgesic is an opiate.

5. The method of claim 1, wherein the pharmaceutical composition further comprises one or more pharmaceutically acceptable excipients to create a transdermal dosage form selected from the group consisting of: gels, ointments, cataplasms, poultices, pastes, creams, lotions, plasters and jellies.

6. A method of transdermally administering cannabidiol through the skin of a subject and into the systemic circulation comprising:
    applying to the skin of the subject a pharmaceutical composition which comprises:
    (i) cannabidiol; and
    (ii) a permeation enhancer consisting of diethylene glycol monoethyl ether.

* * * * *

UNITED STATES PATENT AND TRADEMARK OFFICE
CERTIFICATE OF CORRECTION

PATENT NO.        : 8,449,908 B2
APPLICATION NO.   : 11/157034
DATED             : May 28, 2013
INVENTOR(S)       : Audra L. Stinchcomb and Buchi N. Nalluri Page 1 of 1

It is certified that error appears in the above-identified patent and that said Letters Patent is hereby corrected as shown below:

In the claims

In claim 1:

At column number 20, line number 28, please insert -- (i) -- at the beginning of the line.

Signed and Sealed this
Second Day of August, 2016

Michelle K. Lee
*Director of the United States Patent and Trademark Office*